US008173647B2

(12) United States Patent
Atallah et al.

(10) Patent No.: US 8,173,647 B2
(45) Date of Patent: May 8, 2012

(54) PI 3-KINASE INHIBITORS AND METHODS OF THEIR USE

(76) Inventors: Gordana Atallah, Emeryville, CA (US); Sarah Bartulis, Emeryville, CA (US); Matthew Burger, Emeryville, CA (US); Hanne Merritt, Emeryville, CA (US); Simon Ng, Emeryville, CA (US); Zhi-Jie Ni, Emeryville, CA (US); Sabina Pecchi, Emeryville, CA (US); Keith B. Pfister, Emeryville, CA (US); Aaron Smith, Emeryville, CA (US); Charles Voliva, Emeryville, CA (US); Allan Wagman, Emeryville, CA (US); Yanchen Zhang, Emeryville, CA (US)

( * ) Notice: Subject to any disclaimer, the term of this patent is extended or adjusted under 35 U.S.C. 154(b) by 88 days.

(21) Appl. No.: 12/449,286

(22) PCT Filed: Feb. 6, 2008

(86) PCT No.: PCT/US2008/053190
§ 371 (c)(1),
(2), (4) Date: Oct. 14, 2009

(87) PCT Pub. No.: WO2008/098058
PCT Pub. Date: Aug. 14, 2008

(65) Prior Publication Data
US 2010/0048547 A1 Feb. 25, 2010

(51) Int. Cl.
*A61K 31/5377* (2006.01)
*C07D 413/14* (2006.01)
(52) U.S. Cl. ............ 514/231.5; 544/106; 544/111; 544/122; 514/231.2; 514/232.2
(58) Field of Classification Search .......... 544/106, 544/111, 114, 122; 514/231.2, 231.5, 232.2
See application file for complete search history.

(56) References Cited

U.S. PATENT DOCUMENTS

| | | | |
|---|---|---|---|
| 3,975,384 | A | 8/1976 | Narr |
| 4,929,726 | A | 5/1990 | Strekowski |
| 5,786,355 | A | 7/1998 | Konno |
| 5,976,758 | A | 11/1999 | Fukui |
| 5,990,105 | A | 11/1999 | Bos |
| 6,251,900 | B1 | 6/2001 | Kawashima |
| 6,288,228 | B1 | 9/2001 | Henkin |
| 6,495,558 | B1 | 12/2002 | Armistead |
| 6,599,926 | B2 | 7/2003 | Pinto |
| 6,603,000 | B2 | 8/2003 | Yee |
| 6,743,788 | B2 | 6/2004 | Cirillo |
| 6,846,928 | B2 | 1/2005 | Bebbington |
| 7,423,148 | B2 | 9/2008 | Nuss |
| 2004/0002496 | A1 | 1/2004 | Bebbington |
| 2004/0009974 | A1 | 1/2004 | Bebbington |
| 2004/0009981 | A1 | 1/2004 | Bebbington |
| 2005/0014753 | A1 | 1/2005 | Ding |

FOREIGN PATENT DOCUMENTS

| | | | |
|---|---|---|---|
| DE | | 2341925 A1 | 3/1975 |
| EP | | 0459830 A1 | 12/1991 |
| EP | | 1277738 A1 | 1/2003 |
| EP | | 1277741 A1 | 1/2003 |
| WO | | 0043373 A2 | 7/2000 |
| WO | | 0172745 A1 | 10/2001 |
| WO | | 0183456 A1 | 11/2001 |
| WO | | 0222606 A1 | 3/2002 |
| WO | | 0222608 A1 | 3/2002 |
| WO | | 0236586 A1 | 5/2002 |
| WO | | 02062789 A1 | 8/2002 |
| WO | | 02102313 A2 | 12/2002 |
| WO | | 03030909 A1 | 4/2003 |
| WO | | 2004048365 A1 | 6/2004 |
| WO | WO 2004/048365 | | 6/2004 |
| WO | | 2004084824 A2 | 10/2004 |
| WO | | 2005007648 A2 | 1/2005 |
| WO | | 2005009977 A1 | 2/2005 |
| WO | | 2005028444 A1 | 3/2005 |
| WO | | 2006005914 A1 | 1/2006 |
| WO | WO 2006/005914 | | 1/2006 |
| WO | WO 2006/005915 | | 1/2006 |
| WO | | 2007080382 A1 | 7/2007 |
| WO | WO 2007/080382 | | 7/2007 |
| WO | WO 2007/084786 | | 7/2007 |

OTHER PUBLICATIONS

Pick et al (2007): STN International HCAPLUS database, Columbus (OH), accession No. 2007: 816899.*
Andrisano, R., "Pyrimidine. IV," Bollettino Scientifico della Facolta di Chimica Industriale di Bologna 5:48-51, 1947. Volume Date 1944-1947. CA 44:19897, 1950 (1 page).
Balant, L.P., and E. Doelker, "Metabolic Considerations in Prodrug Design," in M.W. Wolff (ed.), Burger's Medicinal Chemistry and Drug Discovery, vol. 1, Principles and Practice, 5th ed., Wiley, new York, 1995, pp. 975-977.
Banker, G.S. and C.T. Rhodes (eds.), Modern Pharmaceutics, 3rd ed., Marcel Dekker, New York, 1996, pp. 451 and 596. Bennet, J.C. and F. Plum (eds.), Cecil Textbook of Medicine, 20th ed., W.B. Saunders, Philadelphia, 1996, Part XIV, Oncology, pp. 1004-1101.
Brown, D.M., and G.A.R. Kon, "Some Heterocyclic Analogues of Stilbenes," Journal of the Chemical Society, 1948, pp. 2147-2153.
Bundy, G.L., et al., "Synthesis of 2,4-Diaminopyrrolo[2,3-d]pyrimidines Via Thermal Fischer Indolization. Pyrazole Formation with Ytterbium Triflate Catalysis," Journal of Heterocyclic Chemistry 37:1471-1477, Nov.-Dec. 2000.
Bundy, G.L., et al., "Synthesis of Novel 2,4-Diaminopyrrolo[2,3-d]pyrimidines With Antioxidant, neuroprotective, and Antiasthma Activity," Journal of Medicinal Chemistry 38(21):4161-4163, Oct. 1995.

(Continued)

*Primary Examiner* — Golam M M Shameem
(74) *Attorney, Agent, or Firm* — Scott W. Reid

(57) ABSTRACT

Phosphatidylinositol (PI) 3-kinase inhibitor compounds, their pharmaceutically acceptable salts, and prodrugs thereof; compositions of the new compounds, either alone or in combination with at least one additional therapeutic agent, with a pharmaceutically acceptable carrier; and uses of the new compounds, either alone or in combination with at least one additional therapeutic agent, in the prophylaxis or treatment of diseases characterized by the abnormal activity of growth factors, protein serine/threonine kinases, and phospholipid kinases, including proliferative diseases, inflammatory and obstructive airways diseases, allergic conditions, autoimmune and cardiovascular diseases.

6 Claims, No Drawings

OTHER PUBLICATIONS

Cabaj, J.E., et al., "Bromine-Mediated Addition of Nucleophiles to the Electron-Rich Pyrimidine Subunit of Tirilazad," Journal of Organic Chemistry 59(17):5090-5092, Aug. 1994.

Caine, G.J., et al., "Coagulopathic Complications in Breast Cancer," Cancer 98(8):1578-1586, Oct. 2003.

Crowder, R.J., and M.J. Ellis, "Treating Breast Cancer Through Novel Inhibitors of the Phosphatidylinositol 3'-Kinase Pathway," Breast Cancer Research 7(5):212-214, Oct. 2005.

Falco, E.A., et al., "2,4-Diaminopyrimidines. A New Series of Antimalarials," British Journal of Pharmacology and Chemotherapy 6(2):185-200, Jun. 1951. CA 46:27482, 1952 (1 page).

Font, D., et al., "Development of an Efficient and Straightforward Methodology Toward the Synthesis of Molecularly Diverse 2,6-Distributed 3,4-Dihydropyrimidin-4(3H)-ones," Synthesis 13:1833-1842, Sep. 2002.

Kothari, S., et al., "A Facile One Pot Conversion of 3',5'-dibromo-4'-hydroxy Substituted Chalcones to Pyrimidine Derivatives and Their Antibacterial and Herbicidal Activity," Indian Journal of Heterocyclic Chemistry 8(4):285-288, 1999. CA 131:257250, 1999 (1 page).

Kowalewski, A., et al., "Unfused heterobicyles as Amplifiers of Phleomycin. IV. 4,5'-Bipyrimidines With Dimethylamino and/or Dimethylaminoethylamino Substituents," Australian Journal of Chemistry 34(12):2929-2933, 1981.

Li, S.Y., et al., "PIK3CA Mutations in Breast Cancer Are Associated With Poor Outcome," Breast Cancer Research and Treatment 96(1):91-95, Mar. 2006.

Mamaev, V.P., et al., "Reaction Kinetics of Substituted 2-Chloropyrimidines With Piperidine," Reaktsionnaya Sposobnost Organicheskikh Soedinenii 5(3):824-837, 1968. CA 70:76976, 1969 (1 page).

Mikhaleva, M.A., et al, Pyrimidines. 70. Relative Reactivity of the Chlorine Atoms of 2,2',4-Trichloro-4',5-bipyrimidine in the Reaction With Piperidine, Khimiya Geterotsiklicheskikh Soedinenii 6:821-826, 1979. CA 91:107951, 1979 (1 page).

Mokrosz, M.J., et al., "Structure-Activity Relationship Studies of CNS Agents. Part 25: 4,6-Di(hyteroaryl)-2-(N-methylpiperazino)pyrimidines as New, Potent 5-HT2A Receptor Ligands: A Verification of the Topographic Model," Archiv der Pharmazie 328(9):659-666, 1995. CA 124:223, 1995 (1 page).

Nahta, R., et al., "Signal Transduction Inhibitors in the Treatment of Breast Cancer," Current Medicinal Chemistry—Anti-Cancer Agents 3(3):201-216, May 2003.

Ouf, A.A.A., et al., "Preparation fo Some Methyl Pyrimidines Expected to Be Antimetabolites," Egyptian Journal of Pharmaceutical Science 14(2):180-195, 1973.

Sharma, P., et al., "A Convenient One-Pot Synthesis of 2-Substituted-4,6-diaryl Pyrimidines," Indian Journal of Chemistry 38B:966-968, Aug. 1999. CA 132:207818, 2000 (1 page).

Sukhwal, S., et al., "A New Route to 2-Piperidino-4,6-diarylpyrimidines," Indian Journal of Heterocyclic Chemistry 4(1):67-68, 1994. CA 122 105796, 1995 (2 pages).

Tani, H., et al., "2,4,6-Trisubstituted Pyrimidines," JP 49021148, May 30, 1974. CA 82:140173, 1975 (1 page).

Sanjay Babu Katiyar, "Syntheses of 2,4,6-Trisubstituted Pyrimidine Derivatives as a New Class of Antifilarial Topoisomerase II Inhibitors", Bioorganic & Medicinal Chemistry Letters 15 (2005) 47-50, Science Direct.

Katiyar et al., "Syntheses of 2,4,6-Trisubstituted Pyrimidine Derivatives as a New Class of Antifilarial . . . " Bioorganic & Medicinal Chemistry Letters 15(1):47-50, 2005.

Patani, George A. et al., "Bioisosterism: A Rational Approach in Drug Design", Chem. Rev. 1996, vol. 96, No. 8, pp. 3147-3176.

Silverman, Richard B., "The Organic Chemistry of Drug Design and Drug Action", Elsevier Academic Press, 2004, 2nd ed., pp. 29-34.

* cited by examiner

PI 3-KINASE INHIBITORS AND METHODS OF THEIR USE

FIELD OF THE INVENTION

This invention relates to new phosphatidylinositol (PI) 3-kinase inhibitor compounds, their pharmaceutically acceptable salts, and prodrugs thereof. This invention also relates to compositions of these compounds, either alone or in combination with at least one additional therapeutic agent, and optionally in combination with a pharmaceutically acceptable carrier. This invention still further relates to methods of use of these compounds, either alone or in combination with at least one additional therapeutic agent, in the prophylaxis or treatment of a number of diseases, in particular, those mediated by one or more of abnormal activity of growth factors, receptor tyrosine kinases, protein serine/threonine kinases, G protein coupled receptors and phospholipid kinases and phosphatases.

BACKGROUND

Phosphatidylinositol 3-kinases (PI3Ks) comprise a family of lipid kinases that catalyze the transfer of phosphate to the D-3' position of inositol lipids to produce phosphoinositol-3-phosphate (PIP), phosphoinositol-3,4-diphosphate (PIP$_2$) and phosphoinositol-3,4,5-triphosphate (PIP$_3$) that, in turn, act as second messengers in signaling cascades by docking proteins containing pleckstrin-homology, FYVE, Phox and other phospholipid-binding domains into a variety of signaling complexes often at the plasma membrane (Vanhaesebroeck et al., *Annu. Rev. Biochem.* 70:535 (2001); Katso et al., *Annu. Rev. Cell Dev. Biol.* 17:615 (2001)). Of the two Class 1 PI3Ks, Class 1A PI3Ks are heterodimers composed of a catalytic p110 subunit (α, β, δ isoforms) constitutively associated with a regulatory subunit that can be p85α, p55α, p50α, p85β or p55γ. The Class 1B sub-class has one family member, a heterodimer composed of a catalytic p110γ subunit associated with one of two regulatory subunits, p101 or p84 (Fruman et al., *Annu Rev. Biochem.* 67:481 (1998); Suire et al., *Curr. Biol.* 15:566 (2005)). The modular domains of the p85/55/50 subunits include Src Homology (SH2) domains that bind phosphotyrosine residues in a specific sequence context on activated receptor and cytoplasmic tyrosine kinases, resulting in activation and localization of Class 1A PI3Ks. Class 1B PI3K is activated directly by G protein-coupled receptors that bind a diverse repertoire of peptide and non-peptide ligands (Stephens et al., *Cell* 89:105 (1997)); Katso et al., *Annu. Rev. Cell Dev. Biol.* 17:615-675 (2001)). Consequently, the resultant phospholipid products of class I PI3K link upstream receptors with downstream cellular activities including proliferation, survival, chemotaxis, cellular trafficking, motility, metabolism, inflammatory and allergic responses, transcription and translation (Cantley et al., *Cell* 64:281 (1991); Escobedo and Williams, *Nature* 335:85 (1988); Fantl et al., *Cell* 69:413 (1992)).

In many cases, PIP2 and PIP3 recruit Akt, the product of the human homologue of the viral oncogene v-Akt, to the plasma membrane where it acts as a nodal point for many intracellular signaling pathways important for growth and survival (Fantl et al., *Cell* 69:413-423 (1992); Bader et al., *Nature Rev. Cancer* 5:921 (2005); Vivanco and Sawyer, *Nature Rev. Cancer* 2:489 (2002)). Aberrant regulation of PI3K, which often increases survival through Akt activation, is one of the most prevalent events in human cancer and has been shown to occur at multiple levels. The tumor suppressor gene PTEN, which dephosphorylates phosphoinositides at the 3' position of the inositol ring and in so doing antagonizes PI3K activity, is functionally deleted in a variety of tumors. In other tumors, the genes for the p110α isoform, PIK3CA, and for Akt are amplified and increased protein expression of their gene products has been demonstrated in several human cancers. Furthermore, mutations and translocation of p85α that serve to up-regulate the p85-p110 complex have been described in a few human cancers. Finally, somatic missense mutations in PIK3CA that activate downstream signaling pathways have been described at significant frequencies in a wide diversity of human cancers (Kang at el., *Proc. Natl. Acad. Sci. USA* 102:802 (2005); Samuels et al., *Science* 304: 554 (2004); Samuels et al., *Cancer Cell* 7:561-573 (2005)). These observations show that deregulation of phosphoinositol-3 kinase and the upstream and downstream components of this signaling pathway is one of the most common deregulations associated with human cancers and proliferative diseases (Parsons et al., *Nature* 436:792 (2005); Hennessey at el., *Nature Rev. Drug Disc.* 4:988-1004 (2005)).

In view of the above, inhibitors of PI3Ks would be of particular value in the treatment of proliferative disease and other disorders.

SUMMARY OF THE INVENTION

The present invention provides new phosphatidylinositol 3-kinase (PI3K) inhibitor compounds, pharmaceutical formulations that include the compounds, methods of inhibiting phosphatidylinositol 3-kinase (PI3K), and methods of treating disease conditions modulated by PI3K.

In one embodiment, this invention is directed to compounds, stereoisomers, tautomers, or pharmaceutically acceptable salts of Formula I:

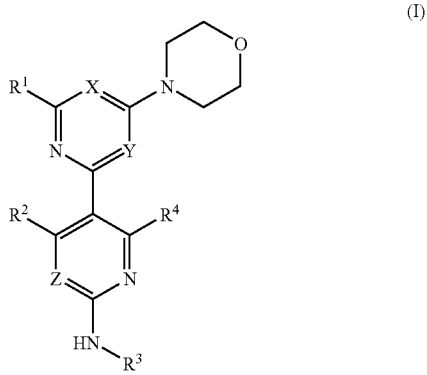

wherein:
X is N and Y is CR$^5$, or Y is N and X is CR$^5$;
Z is N or CR$^6$;
R$^1$ is selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfoxide, substituted sulfoxide, sulfonylamino, substituted sulfonylamino, sulfonyloxy, substituted sulfonyloxy, thioacyl, thiol, alkylthio, and substituted alkylthio, provided that when X is N, $R^1$ is not morpholino;

$R^2$ and $R^4$, are each independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, and substituted alkylthio;

$R^3$ is selected from the group consisting of hydrogen, alkyl, —CO—$R^{3a}$, substituted alkyl, a three- to seven-membered cycloalkyl or a three- to seven-membered substituted cycloalkyl ring, and a four- to seven-membered heterocyclyl or a four- to seven-membered substituted heterocyclyl ring; and $R^{3a}$ is selected from the group consisting of alkyl, substituted alkyl, alkoxy, substituted alkoxy, amino, substituted amino, and alkylamino; and $R^5$ is selected from the group consisting of hydrogen, cyano, nitro, halogen, hydroxy, amino, substituted amino, alkyl, substituted alkyl, —$COR^{5a}$, and —$NR^{5a}COR^{5b}$, wherein $R^{5a}$, and $R^{5b}$ are independently selected from the group consisting of hydrogen, and substituted or unsubstituted alkyl; and $R^6$ is selected from the group consisting of hydrogen, C1-3 alkyl, substituted C1-3 alkyl, methoxy, trifluoromethyl, cycloalkyl, substituted alkyl, acyl, acylamino, acyloxy, amino, substituted amino, aminocarbonyl, aminosulfonyl, carboxyl, carboxyl ester, cyano, halo, hydroxy, nitro, SO3H, sulfonyl, substituted sulfonyl, sulfoxide, substituted sulfoxide, sulfonyloxy, thioacyl, thiol and methylthio.

In some embodiments, the invention is directed to compounds, stereoisomers, tautomers, or pharmaceutically acceptable salts of Formula II and the related compositions and methods wherein Formula II is:

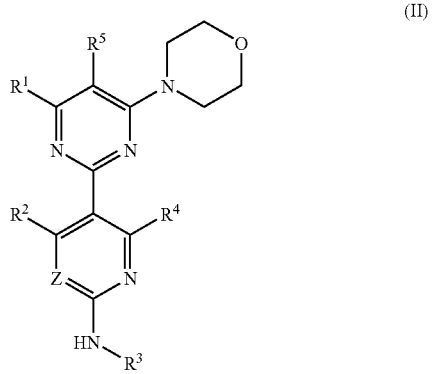

(II)

wherein:

Z is N or $CR^6$;

$R^1$ is selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfoxide, substituted sulfoxide, sulfonylamino, substituted sulfonylamino, sulfonyloxy, substituted sulfonyloxy, thioacyl, thiol, alkylthio, and substituted alkylthio;

$R^2$ and $R^4$, are each independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acylamino, acyloxy, amino, substituted amino, aminocarbonyl, aminothiocarbonyl, aminocarbonylamino, aminothiocarbonyl-amino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, and substituted alkylthio;

$R^3$ is selected from the group consisting of hydrogen, alkyl, —CO—$R^{3a}$, substituted alkyl, a three- to seven-membered cycloalkyl or a three- to seven-membered substituted cycloalkyl ring, and a four- to seven-membered heterocyclyl or a four- to seven-membered substituted heterocyclyl ring; and $R^{3a}$ is selected from the group consisting of alkyl, substituted alkyl, alkoxy, substituted alkoxy, amino, substituted amino, and alkylamino; and $R^5$ is selected from the group consisting of hydrogen, cyano, nitro, halogen, hydroxy, amino, substituted amino, alkyl, substituted alkyl, —$COR^{5a}$, and —$NR^{5a}COR^{5b}$, wherein $R^{5a}$, and $R^{5b}$ are independently selected from the group consisting of hydrogen, and substituted or unsubstituted alkyl; and $R^6$ is selected from the group consisting of hydrogen, C1-3 alkyl, substituted C1-3 alkyl, methoxy, trifluoromethyl, cycloalkyl, substituted alkyl, acyl, acylamino, acyloxy, amino, substituted amino, aminocarbonyl, aminosulfonyl, carboxyl, carboxyl ester, cyano, halo, hydroxy, nitro, SO3H, sulfonyl, substituted sulfonyl, sulfoxide, substituted sulfoxide, sulfonyloxy, thioacyl, thiol and methylthio.

In other embodiments, the invention is directed to compounds, stereoisomers, tautomers, or pharmaceutically acceptable salts of Formula III and the related compositions and methods wherein Formula III is:

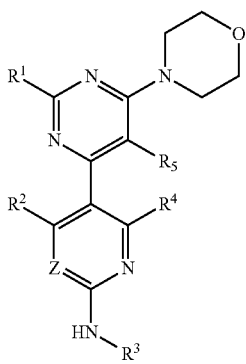

(III)

wherein,

Z is N or CR⁶;

R¹ is selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO₃H, sulfonyl, substituted sulfonyl, sulfoxide, substituted sulfoxide, sulfonylamino, substituted sulfonylamino, sulfonyloxy, substituted sulfonyloxy, thioacyl, thiol, alkylthio, and substituted alkylthio, provided that R¹ is not morpholino;

R² and R⁴, are each independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO₃H, sulfonyl, substituted sulfonyl, sulfonyloxy, thioacyl, thiol, alkylthio, and substituted alkylthio;

R³ is selected from the group consisting of hydrogen, alkyl, —CO—R³ᵃ, substituted alkyl, a three- to seven-membered cycloalkyl or a three- to seven-membered substituted cycloalkyl ring, and a four- to seven-membered heterocyclyl or a four- to seven-membered substituted heterocyclyl ring; and R³ᵃ is selected from the group consisting of alkyl, substituted alkyl, alkoxy, substituted alkoxy, amino, substituted amino, and alkylamino; and R⁵ is selected from the group consisting of hydrogen, cyano, nitro, halogen, hydroxy, amino, substituted amino, alkyl, substituted alkyl, —COR⁵ᵃ, and —NR⁵ᵃCOR⁵ᵇ, wherein R⁵ᵃ, and R⁵ᵇ are independently selected from the group consisting of hydrogen, and substituted or unsubstituted alkyl; and R⁶ is selected from the group consisting of hydrogen, C1-3 alkyl, substituted C1-3 alkyl, methoxy, trifluoromethyl, cycloalkyl, substituted alkyl, acyl, acylamino, acyloxy, amino, substituted amino, aminocarbonyl, aminosulfonyl, carboxyl, carboxyl ester, cyano, halo, hydroxy, nitro, SO3H, sulfonyl, substituted sulfonyl, sulfoxide, substituted sulfoxide, sulfonyloxy, thioacyl, thiol and methylthio.

In other embodiments of the invention, compounds, stereoisomers, tautomers, or pharmaceutically acceptable salts of Formulas I, II or III are provided wherein R¹ is not substituted or unsubstituted phenyl.

Other embodiments of the invention provide for a pharmaceutical composition comprising a pharmaceutically acceptable carrier and a therapeutically effective amount of compound of Formulas I, II or III, as defined above, or a stereoisomer, tautomer, or pharmaceutically acceptable salt thereof.

Yet other embodiments of the invention provide for methods of treating disease conditions modulated by PI3K activity, by administering to a patient in need thereof a therapeutically effective amount of a compound of formulas I, II or III, as defined above, either alone or in combination with at least one additional therapeutically active agent.

DETAILED DESCRIPTION

Phosphatidylinositol-3-kinase (PI3K) mediates the signal from various growth factors to regulate cell proliferation and survival. A Serine/Threonine (Ser/Thr, or S/T) protein kinase, termed Akt, is identified as a downstream target of PI 3-kinase. This protein kinase is recruited to the cell membrane by interaction of its pleckstrin homology domain with PI3K products, phosphatidylinositol-3,4,5-triphosphate (PIP₃), and phosphatidylinositol-3,4-diphosphate (PIP₂), where it is activated by phosphorylation of its catalytic domain by 3-Phosphoinositide-dependent Kinase-1 (PDK-1). Akt is further activated by phosphorylation of a serine in its C-terminal hydrophobic motif by another kinase (PDK-2). The activation of Akt acts downstream to regulate additional kinases many of which are implicated in cellular processes that control survival, proliferation, metabolism and growth translation. PI3K can also drive cellular processes that impact transformation, cellular proliferation, cytoskeletal rearrangement and survival through a parallel pathway that does not involve Akt (Hennessy et al., *Nat. Rev. Drug Disc.* 4:988-1004 (2005)). Two of these pathways are activation of the small GTP-binding proteins Cdc42 and Rac1 and activation of the serum and glucocorticoid-inducible kinase (SGK). Cdc42 and Rac1, which regulate cytoskeletal movement and cell motility and can function as oncogenes when over-expressed, are also linked to the RAS pathway. Thus, PI3K activity generates 3'-phosphatidylinositol lipids that act as a nodal point to stimulate a diversity of downstream signaling pathways.

That these pathways impact cellular properties proliferation, survival, motility and morphology that are often disrupted in cancer, proliferative diseases, thrombotic diseases and inflammation, among others, dictates that compounds inhibiting PI3K (and isoforms thereof) have utility, either as a single agent or in combination, in the treatment of these diseases. In cancer, deregulation of the PI3K/Akt pathway is extensively documented, including overexpression of the PIK3CA gene, activating mutations of the PIK3CA gene, overexpression of Akt, mutations of PDK-1, and deletions/ inactivation of PTEN (Parsons et al., *Nature* 436:792 (2005); Hennessy et al., *Nat. Rev. Drug Disc.* 4:988 (2005); Stephens et al., *Curr. Opin. Pharmacol.* 5:1 (2005); Bonneau and Longy, *Human Mutation* 16:109 (2000) and Ali et al., *J. Natl. Can. Inst.* 91:1922 (1999)). Recent findings indicate that PIK3CA is frequently mutated (>30%) in various solid tumors in humans (Samuels and Ericson, *Curr. Opin. Oncology* 18:77 (2005)) and the most frequent of these mutations promote cell growth and invasion (Samuels et al., *Cancer Cell* 7:561 (2005), and are transforming (Kang et al., *Proc. Natl. Acad. Sci. USA* 102:802 (2005), Zhao et al., *Proc. Natl. Acad. Sci. USA* 102:18443 (2005)). Thus, inhibitors of PI3K, particularly of the p110α isoform encoded by PIK3CA and its mutations, will be useful in the treatment of cancers driven by these mutations and deregulations.

In its compounds aspects, the embodiments provide novel compounds that act as inhibitors of protein or lipid kinases, more particularly as inhibitors of serine/threonine kinases and/or lipid kinases, and, even more particularly, as inhibitors of phosphatidylinositol 3-kinase (PI3K) function. The compounds provided herein can be formulated into pharmaceutical formulations that are useful in treating patients with a need for an inhibitor of PI3K, or of the catalytic p110α isoform subunit or a variant thereof, especially, in particular embodiments, to provide compositions and methods for reducing cellular proliferation and increasing cell death in the treatment of cancer.

Throughout this application, the text refers to various embodiments of the present compounds, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

Definitions

The terms used in the claims are defined below.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cyanate, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiocyanate, thiol, alkylthio, and substituted alkylthio, wherein said substituents are defined herein.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O), substituted alkenyl-C(O), alkynyl-C(O), substituted alkynyl-C(O)—, cycloalkyl-C(O)—, substituted cycloalkyl-C(O), cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Acyl includes the "acetyl" group $CH_3C(O)$—.

"Acylamino" refers to the groups —NRC(O)alkyl, —NRC(O) substituted alkyl, —NRC(O)cycloalkyl, —NRC(O) substituted cycloalkyl, —NRC(O)cycloalkenyl, —NRC(O) substituted cycloalkenyl, —NRC(O)alkenyl, —NRC(O) substituted alkenyl, —NRC(O)alkynyl, —NRC(O) substituted alkynyl, —NRC(O)aryl, —NRC(O) substituted aryl, —NRC(O)heteroaryl, —NRC(O) substituted heteroaryl, —NRC(O)heterocyclic, and —NRC(O) substituted heterocyclic wherein R is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"Amino" refers to the group —$NH_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-cycloalkenyl, —$SO_2$-substituted cylcoalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein. When R' is hydrogen and R" is alkyl, the substituted amino group is sometimes referred to herein as alkylamino. When R' and R" are alkyl, the substituted amino group is sometimes referred to herein as dialkylamino. When referring to a mono-substituted amino, it is meant that either R' or R" is hydrogen but not both. When referring to a disubstituted amino, it is meant that neither R' nor R" are hydrogen.

"Hydroxyamino" refers to the group —NHOH.

"Alkoxyamino" refers to the group —NHO-alkyl wherein alkyl is defined herein.

"Aminocarbonyl" refers to the group —C(O)NR$^{10}$R$^{11}$ where R$^{10}$ and R$^{11}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{10}$ and R$^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonyl" refers to the group —C(S)NR$^{10}$R$^{11}$ where R$^{10}$ and R$^{11}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{10}$ and R$^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonylamino" refers to the group —NRC(O)NR$^{10}$R$^{11}$ where R is hydrogen or alkyl and R$^{10}$ and R$^{11}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{10}$ and R$^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonylamino" refers to the group —NRC(S)NR$^{10}$R$^{11}$ where R is hydrogen or alkyl and R$^{10}$ and R$^{11}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{10}$ and R$^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonyloxy" refers to the group —O—C(O)NR$^{10}$R$^{11}$ where R$^{10}$ and R$^{11}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{10}$ and R$^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyl" refers to the group —SO$_2$NR$^{10}$R$^{11}$ where R$^{10}$ and R$^{11}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{10}$ and R$^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyloxy" refers to the group —O—SO2NR10R11 where R10 and R11 are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where R$^{10}$ and R$^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonylamino" refers to the group —NR—SO$_2$NR$^{10}$R$^{11}$ where R is hydrogen or alkyl and R$^{10}$ and R$^{11}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkyenyl, heteroaryl, substituted heteroaryl, heterocyclyl, and substituted heterocyclyl and where R$^{10}$ and R$^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkyenyl, aryl, substituted aryl, heteroaryl, substituted heteroaryl, heterocyclic and substituted heterocyclic are as defined herein.

"Amidino" refers to the group —C(=NR$^{12}$)R$^{10}$R$^{11}$ where R$^{10}$, R$^{11}$, and R$^{12}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclyl, and substituted heterocyclyl and where $R^{10}$ and $R^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cyanate, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiocyanate, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified, for example, by vinyl, allyl, and but-3-en-1-yl.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxy substitution is not attached to a vinyl (unsaturated) carbon atom.

"Alkynyl" refers to alkynyl groups having from 2 to 6 carbon atoms and preferably 2 to 3 carbon atoms and having at least 1 and preferably from 1 to 2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxy substitution is not attached to an acetylenic carbon atom.

"Azido" refers to the group —$N_3$.

"Hydrazino" refers to the group —$NHNH_2$.

"Substituted hydrazino" refers to the group —NRNR'R" where R, R', and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-cycloalkenyl, —$SO_2$-substituted cylcoalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"Cyanate" refers to the group OCN⁻.

"Thiocyanate" refers to the group SCN⁻.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"(Carboxyl ester)amino" refers to the group —NR—C(O)O-alkyl, substituted —NR—C(O)O-alkyl, —NR—C(O)O-alkenyl, —NR—C(O)O-substituted alkenyl, —NR—C(O)O-alkynyl, —NR—C(O)O-substituted alkynyl, —NR—C(O)O-aryl, —NR—C(O)O-substituted aryl, —NR—C(O)O-cycloalkyl, —NR—C(O)O-substituted cycloalkyl, —NR—C(O)O-cycloalkenyl, —NR—C(O)O-substituted cycloalkenyl, —NR—C(O)O-heteroaryl, —NR—C(O)O-substituted heteroaryl, —NR—C(O)O-heterocyclic, and —NR—C(O)O-substituted heterocyclic wherein R is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"(Carboxyl ester)oxy" refers to the group —O—C(O)O-alkyl, substituted —O—C(O)O-alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl, and substituted heterocyclyl are as defined herein.

"Cyano" and "carbonitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C=C<ring unsaturation and preferably from 1 to 2 sites of >C=C<ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, azido, carboxyl, carboxyl ester, (carboxyl ester)amino, (carboxyl ester)oxy, cyano, cyanate, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, hydroxyamino, alkoxyamino, hydrazino, substituted hydrazino, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiocyanate, thiol, alkylthio, and substituted alkylthio, wherein said substituents are defined herein.

"Cycloalkyloxy" refers to —O-cycloalkyl.

"Substituted cycloalkyloxy refers to —O-substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy refers to —O-(substituted cycloalkenyl).

"Cycloalkenylthio" refers to —S-cycloalkenyl.

"Substituted cycloalkenylthio" refers to —S-substituted cycloalkenyl).

"Guanidino" refers to the group —NHC(=NH)NH₂.

"Substituted guanidino" refers to —NR¹³C(=NR¹³)N(R¹³)₂ where each $R^{13}$ is independently selected from the group consisting of hydrogen, alkyl, substituted alkyl, aryl, substituted aryl, heteroaryl, substituted heteroaryl, heterocyclyl, and substituted heterocyclyl and two $R^{13}$ groups attached to a common guanidino nitrogen atom are optionally joined together with the nitrogen bound thereto to form a heterocyclic or substituted heterocyclic group, provided that at least one $R^{13}$ is not hydrogen, and wherein said substituents are as defined herein.

"Halo" or "halogen" refers to fluoro, chloro, bromo and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or unsaturated group having a single ring or multiple condensed rings, including fused bridged and spiro ring systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocyclyl.

"Substituted heterocyclyloxy" refers to the group —O-(substituted heterocyclyl).

"Heterocyclylthio" refers to the group —S-heterocyclyl.

"Substituted heterocyclylthio" refers to the group —S-(substituted heterocyclyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —NO$_2$.

"Oxo" refers to the atom (=O).

"Spirocycloalkyl" refers to divalent cyclic groups from 3 to 10 carbon atoms having a cycloalkyl ring with a spiro union (the union formed by a single atom which is the only common member of the rings) as exemplified by the following structure:

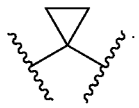

"Spirocyclyl" refers to divalent cyclic groups having a cycloalkyl or heterocyclyl ring with a spiro union, as described for spirocycloalkyl.

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cycloalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—.

"Sulfoxide" refers to the divalent group —S(O)—.

"Substituted sulfonyl" refers to the group —SO-alkyl, —SO-substituted alkyl, —SO-alkenyl, —SO-substituted alkenyl, —SO-cycloalkyl, —SO-substituted cycloalkyl, —SO-cycloalkenyl, —SO-substituted cycloalkenyl, —SO-aryl, —SO-substituted aryl, —SO-heteroaryl, —SO-substituted heteroaryl, —SO-heterocyclic, —SO-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfoxide includes groups such as methyl-SO—, phenyl-SO—, and 4-methylphenyl-SO—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cycloalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thiol" refers to the group —SH.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein.

"Stereoisomer" or "stereoisomers" refer to compounds that differ in the chirality of one or more stereocenters. Stereoisomers include enantiomers and diastereomers.

"Tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Patient" refers to mammals and includes humans and non-human mammals.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate.

"Prodrug" refers to any derivative of a compound of this invention that is capable of directly or indirectly providing a compound of this invention or an active metabolite or residue thereof when administered to a subject. Particularly favored derivatives and prodrugs are those that increase the bioavailability of the compounds of this invention when such compounds are administered to a subject (e.g., by allowing an orally administered compound to be more readily absorbed into the blood) or which enhance delivery of the parent compound to a biological compartment (e.g., the brain or lymphatic system) relative to the parent species. Prodrugs include ester forms of the compounds of the invention. Examples of ester prodrugs include formate, acetate, propionate, butyrate, acrylate, and ethylsuccinate derivatives. An general overview of prodrugs is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

Unless indicated otherwise, the nomenclature of substituents that are not explicitly defined herein are arrived at by naming the terminal portion of the functionality followed by the adjacent functionality toward the point of attachment. For example, the substituent "arylalkyloxycabonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

Some embodiments of the invention are directed to compounds, stereoisomers, tautomers, or pharmaceutically acceptable salts of Formula I and the related compositions and methods wherein Formula I is:

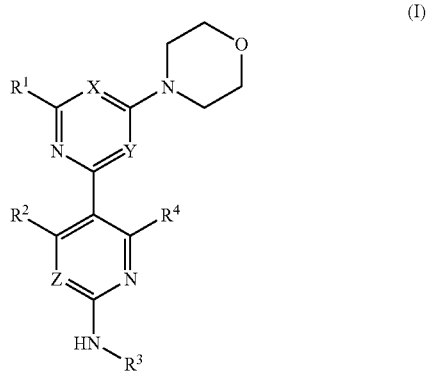

(I)

wherein:
X is N and Y is $CR^5$, or Y is N and X is $CR^5$;
Z is N or $CR^6$;
$R^1$ is selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfoxide, substituted sulfoxide, sulfonylamino, substituted sulfonylamino, sulfonyloxy, substituted sulfonyloxy, thioacyl, thiol, alkylthio, and substituted alkylthio, provided that when X is N, $R^1$ is not morpholino;
$R^2$ and $R^4$, are each independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acylamino, acyloxy, amino, substituted amino, aminocarbonyl, aminothiocarbonyl, aminocarbonylamino, aminothiocarbony-lamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, and substituted alkylthio;
$R^3$ is selected from the group consisting of hydrogen, alkyl, —CO—$R^{3a}$, substituted alkyl, a three- to seven-membered cycloalkyl or a three- to seven-membered substituted cycloalkyl ring, and a four- to seven-membered heterocyclyl or a four- to seven-membered substituted heterocyclyl ring; and
$R^{3a}$ is selected from the group consisting of alkyl, substituted alkyl, alkoxy, substituted alkoxy, amino, substituted amino, and alkylamino; and
$R^5$ is selected from the group consisting of hydrogen, cyano, nitro, halogen, hydroxy, amino, substituted amino, alkyl, substituted alkyl, —$COR^5A$, and —$NR^{5a}COR^{5b}$, wherein $R^{5a}$, and $R^{5b}$ are independently selected from the group consisting of hydrogen, and substituted or unsubstituted alkyl; and
$R^6$ is selected from the group consisting of hydrogen, C1-3 alkyl, substituted C1-3 alkyl, methoxy, trifluoromethyl, cycloalkyl, substituted alkyl, acyl, acylamino, acyloxy, amino, substituted amino, aminocarbonyl, aminosulfonyl, carboxyl, carboxyl ester, cyano, halo, hydroxy, nitro, SO3H, sulfonyl, substituted sulfonyl, sulfoxide, substituted sulfoxide, sulfonyloxy, thioacyl, thiol and methylthio.

In some representative embodiments, the invention provides for compounds of Formula I wherein Y is N and X is $CR^5$.

In some embodiments, the invention provides for compounds of Formula I wherein Z is N.

In some embodiments, the invention provides for compounds of Formula I wherein Z is $CR^6$.

In some embodiments, the invention provides for compounds of Formula I wherein $R^1$ is selected from the group consisting of aryl, substituted aryl, heteroaryl, substituted heteroaryl, heterocyclyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, amino and substituted amino.

In some embodiments, the invention provides for compounds of Formula I wherein $R^1$ is selected from the group consisting of morpholino, tetrahydropyranyloxy and methoxypyridinylamino, provided that when X is N, $R^1$ is not morpholino.

In some embodiments, the invention provides for compounds of Formula I wherein $R^1$ is selected from the group consisting of $-CO_2R_{1a}$, $-NR_{1a}R_{1b}$, $-NR_{1a}SO_2R_{1b}$, $-SOR_{1a}$, $-SO_2R_{1a}$, and $-SO_2NR_{1a}R_{1b}$, wherein $R^{1a}$, and $R^{1b}$ are independently selected from the group consisting of hydrogen, substituted or unsubstituted alkyl, substituted and unsubstituted aryl, substituted and unsubstituted heteroaryl, substituted and unsubstituted heterocyclyl, and substituted and unsubstituted cycloalkyl.

In some embodiments, the invention provides for compounds of Formula I wherein $R^1$ is not substituted or unsubstituted phenyl.

In some embodiments, the invention provides for compounds of Formula I wherein $R^2$ is selected from the group consisting of trifluoromethyl, amino and oxo.

In some embodiments, the invention provides for compounds of Formula I wherein $R^3$ is hydrogen.

In some embodiments, the invention provides for compounds of Formula I wherein $R^4$ is hydrogen.

In some embodiments, the invention provides for compounds of Formula I wherein $R^5$ is hydrogen.

In some embodiments, the invention provides for compounds of Formula I wherein $R^6$ is hydrogen.

Other embodiments provide a compound of Formula II, a stereoisomer, tautomer, or pharmaceutically acceptable salt thereof:

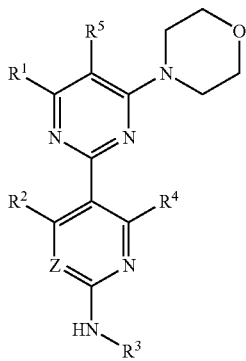

(II)

wherein:
Z is N or $CR^6$;
$R^1$ is selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfoxide, substituted sulfoxide, sulfonylamino, substituted sulfonylamino, sulfonyloxy, substituted sulfonyloxy, thioacyl, thiol, alkylthio, and substituted alkylthio;

$R^2$ and $R^4$, are each independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acylamino, acyloxy, amino, substituted amino, aminocarbonyl, aminothiocarbonyl, aminocarbonylamino, aminothiocarbonyl-amino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, and substituted alkylthio;

$R^3$ is selected from the group consisting of hydrogen, alkyl, $-CO-R^{3a}$, substituted alkyl, a three- to seven-membered cycloalkyl or a three- to seven-membered substituted cycloalkyl ring, and a four- to seven-membered heterocyclyl or a four- to seven-membered substituted heterocyclyl ring; and $R^{3a}$ is selected from the group consisting of alkyl, substituted alkyl, alkoxy, substituted alkoxy, amino, substituted amino, and alkylamino; and $R^5$ is selected from the group consisting of hydrogen, cyano, nitro, halogen, hydroxy, amino, substituted amino, alkyl, substituted alkyl, $-COR^{5a}$, and $-NR^{5a}COR^{5b}$, wherein $R^{5a}$, and $R^{5b}$ are independently selected from the group consisting of hydrogen, and substituted or unsubstituted alkyl; and $R^6$ is selected from the group consisting of hydrogen, C1-3 alkyl, substituted C1-3 alkyl, methoxy, trifluoromethyl, cycloalkyl, substituted alkyl, acyl, acylamino, acyloxy, amino, substituted amino, aminocarbonyl, aminosulfonyl, carboxyl, carboxyl ester, cyano, halo, hydroxy, nitro, SO3H, sulfonyl, substituted sulfonyl, sulfoxide, substituted sulfoxide, sulfonyloxy, thioacyl, thiol and methylthio.

In some embodiments, the invention provides for compounds of Formula II wherein Z is N.

In some embodiments, the invention provides for compounds of Formula II wherein Z is $CR^6$.

In some embodiments, the invention provides for compounds of Formula II wherein $R^1$ is selected from the group consisting of aryl, substituted aryl, heteroaryl, substituted heteroaryl, heterocyclyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, amino and substituted amino.

In some embodiments, the invention provides for compounds of Formula II wherein $R^1$ is selected from the group consisting of morpholino, tetrahydropyranyloxy and methoxypyridinylamino.

In some embodiments, the invention provides for compounds of Formula II wherein $R^1$ is selected from the group consisting of —CO$_2$R$_{1a}$, —NR$_{1a}$R$_{1b}$, —NR$_{1a}$SO$_2$R$_{1b}$, —SOR$_{1a}$, —SO$_2$R$_{1a}$, and —SO$_2$NR$_{1a}$R$_{1b}$, wherein R$_{1a}$ and R$_{1b}$ are independently selected from the group consisting of hydrogen, substituted or unsubstituted alkyl, substituted and unsubstituted aryl, substituted and unsubstituted heteroaryl, substituted and unsubstituted heterocyclyl, and substituted and unsubstituted cycloalkyl.

In some embodiments, the invention provides for compounds of Formula II wherein R$^1$ is not substituted or unsubstituted phenyl.

In some embodiments, the invention provides for compounds of Formula II wherein R$^2$ is selected from the group consisting of trifluoromethyl, amino and oxo.

In some embodiments, the invention provides for compounds of Formula II wherein R$^3$ is hydrogen.

In some embodiments, the invention provides for compounds of Formula II wherein R$^4$ is hydrogen.

In some embodiments, the invention provides for compounds of Formula II wherein R$^5$ is hydrogen.

In some embodiments, the invention provides for compounds of Formula II wherein R$^6$ is hydrogen.

In other embodiments a compound of Formula III, a stereoisomer, tautomer, or pharmaceutically acceptable salt thereof, is provided:

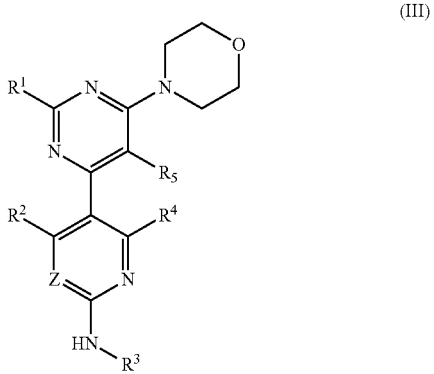

(III)

wherein,

Z is N or CR$^6$;

R$^1$ is selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO$_3$H, sulfonyl, substituted sulfonyl, sulfoxide, substituted sulfoxide, sulfonylamino, substituted sulfonylamino, sulfonyloxy, substituted-sulfonyloxy, thioacyl, thiol, alkylthio, and substituted alkylthio, provided that R$^1$ is not morpholino;

R$^2$ and R$^4$, are each independently selected from the group consisting of hydrogen, alkyl, substituted alkyl, alkenyl, substituted alkenyl, alkynyl, substituted alkynyl, alkoxy, substituted alkoxy, aryl, substituted aryl, heteroaryl, substituted heteroaryl, heterocyclyl, cycloalkyl, substituted cycloalkyl, substituted heterocyclyl, aryloxy, substituted aryloxy, heteroaryloxy, substituted heteroaryloxy, heterocyclyloxy, substituted heterocyclyloxy, cycloalkyloxy, substituted cycloalkyloxy; acyl, acylamino, acyloxy, amino, substituted amino, aminocarbonyl, aminothiocarbonyl, aminocarbonylamino, aminothiocarbonyl-amino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO$_3$H, sulfonyl, substituted sulfonyl, sulfonyloxy, thioacyl, thiol, alkylthio, and substituted alkylthio;

R$^3$ is selected from the group consisting of hydrogen, alkyl, —CO—R$^{3a}$, substituted alkyl, a three- to seven-membered cycloalkyl or a three- to seven-membered substituted cycloalkyl ring, and a four- to seven-membered heterocyclyl or a four- to seven-membered substituted heterocyclyl ring; and R$^{3a}$ is selected from the group consisting of alkyl, substituted alkyl, alkoxy, substituted alkoxy, amino, substituted amino, and alkylamino; and R$^5$ is selected from the group consisting of hydrogen, cyano, nitro, halogen, hydroxy, amino, substituted amino, alkyl, substituted alkyl, —COR$^{5a}$, and —NR$^{5a}$COR$^{5b}$, wherein R$^{5a}$, and R$^{5b}$ are independently selected from the group consisting of hydrogen, and substituted or unsubstituted alkyl; and R$^6$ is selected from the group consisting of hydrogen, C1-3 alkyl, substituted C1-3 alkyl, methoxy, trifluoromethyl, cycloalkyl, substituted alkyl, acyl, acylamino, acyloxy, amino, substituted amino, aminocarbonyl, aminosulfonyl, carboxyl, carboxyl ester, cyano, halo, hydroxy, nitro, SO3H, sulfonyl, substituted sulfonyl, sulfoxide, substituted sulfoxide, sulfonyloxy, thioacyl, thiol and methylthio.

In some embodiments, the invention provides for compounds of Formula III wherein Z is N.

In some embodiments, the invention provides for compounds of Formula III wherein Z is CR$^6$.

In some embodiments, the invention provides for compounds of Formula III wherein R$^1$ is heteroaryl.

In some embodiments, the invention provides for compounds of Formula III wherein R$^1$ is selected from the group consisting of —CO$_2$R$_{1a}$, —NR$_{1a}$R$_{1b}$, —NR$_{1a}$SO$_2$R$_{1b}$, —SOR$_{1a}$, —SO$_2$R$_{1a}$, and —SO$_2$NR$_{1a}$R$_{1b}$, wherein R$_{1a}$ and R$_{1b}$ are independently selected from the group consisting of hydrogen, substituted or unsubstituted alkyl, substituted and unsubstituted aryl, substituted and unsubstituted heteroaryl, substituted and unsubstituted heterocyclyl, and substituted and unsubstituted cycloalkyl.

In some embodiments, the invention provides for compounds of Formula III wherein R$^1$ is not substituted or unsubstituted phenyl.

In some embodiments, the invention provides for compounds of Formula III wherein R$^2$ is selected from the group consisting of trifluoromethyl, amino and oxo.

In some embodiments, the invention provides for compounds of Formula III wherein R$^3$ is hydrogen.

In some embodiments, the invention provides for compounds of Formula III wherein R$^4$ is hydrogen.

In some embodiments, the invention provides for compounds of Formula III wherein R$^5$ is hydrogen.

In some embodiments, the invention provides for compounds of Formula III wherein R$^6$ is hydrogen.

In other representative embodiments, the invention provides for compounds of Formulas I, II and/or III selected from the group consisting of 5-(4-morpholino-6-(tetrahydro-2H-pyran-4-yloxy)pyrimidin-2-yl)-4-(trifluoromethyl)pyridin-2-amine, 4-morpholino-6-(tetrahydro-2H-pyran-4-yloxy)-4'-(trifluoromethyl)-2,5'-bipyrimidin-2'-amine, 4-morpholino-6-tetrahydro-2H-pyran-4-yloxy)-2,5'-bipyrimidine-2',4'-diamine, 2-amino-5-(4-morpholino-6-(tetrahydro-2H-pyran-4-yloxy)pyrimidin-2-yl)pyrimidin-4(3H)-one, 2-(6-amino-4-(trifluoromethyl)pyridin-3-yl)-N-(6-methoxy-pyridin-3-yl)-6-morpholinopyrimidin-4-amine, N4-(6-methoxypyridin-3-yl)-6-morpholino-4'-(trifluoromethyl)-2,5'-bipyrimidine-2',4-diamine, N4-(6-methoxypyridin-3-yl)-6-morpholino-2,5'-bipyrimidine-2',4,4'-triamine, 2-amino-5-(4-(6-methoxypyridin-3-ylamino)-6-morpholinopyrimidin-2-yl)pyrimidin-4(3H)-one, 5-(4,6-dimorpholino-pyrimidin-2-yl)-4-(trifluoromethyl)pyridin-2-amine, 4,6-dimorpholino-4'-(trifluoro-methyl)-2,5'-bipyrimidin-2'-amine, 4,6-dimorpholino-2,5'-bipyrimidine-2',4'-diamine, and the stereoisomers, tautomers, and pharmaceutically acceptable salts thereof.

In other embodiments, the invention provides for pharmaceutical compositions comprising a pharmaceutically acceptable carrier and a therapeutically effective amount of a compound of Formula I, II or III, or a stereoisomer, tautomer, or pharmaceutically acceptable salt thereof.

In other embodiments, the pharmaceutical composition comprises a compound is selected from the group consisting of 5-(4-morpholino-6-(tetrahydro-2H-pyran-4-yloxy)pyrimidin-2-yl)-4-(trifluoromethyl)pyridin-2-amine, 4-morpholino-6-(tetrahydro-2H-pyran-4-yloxy)-4'-(trifluoromethyl)-2,5'-bipyrimidin-2'-amine, 4-morpho-lino-6-(tetrahydro-2H-pyran-4-yloxy)-2,5'-bipyrimidine-2',4'-diamine, 2-amino-5-(4-morpholino-6-(tetrahydro-2H-pyran-4-yloxy)pyrimidin-2-yl)pyrimidin-4(3H)-one, 2-(6-amino-4-(trifluoromethyl)pyridin-3-yl)-N-(6-methoxypyridin-3-yl)-6-morpholino-pyrimidin-4-amine, N4-(6-methoxypyridin-3-yl)-6-morpholino-4'-(trifluoromethyl)-2,5'-bipyrimidine-2',4-diamine, N4-(6-methoxypyridin-3-yl)-6-morpholino-2,5'-bipyrimidine-2',4,4'-triamine, 2-amino-5-(4-(6-methoxypyridin-3-ylamino)-6-morpholinopyrimidin-2-yl)pyrimidin-4(3H)-one, 5-(4,6-dimorpholinopyrimidin-2-yl)-4-(trifluoromethyl)-pyridin-2-amine, 4,6-dimorpholino-4'-(trifluoromethyl)-2,5'-bipyrimidin-2'-amine, 4,6-dimorpholino-2,5'-bipyrimidine-2',4'-diamine, 6-morpholino-$N^2$-(quinolin-3-yl)-4,5'-bi-pyrimidine-2,2'-diamine, 2-(2H-benzo[b][1,4]oxazin-4(3H)-yl)-6-morpholino-4,5'-bi-pyrimidin-2'-amine, 6-morpholino-$N^2$-(3-(trifluoromethyl)pyridin-4-yl)-4,5'-bi-pyrmidine-2,2'-diamine, 7-(2'-amino-6-morpholino-4,5'-bipyrimidin-2-ylamino)-2H-benzo[b][1,4]oxazin-3(4H)-one, 6-morpholino-$N^2$-(8-(trifluoromethyl)quinolin-4-yl)-4,5'-bipyrimidine-2,2'-diamine, 2-(3,4-dihydroquinolin-1(2H)-yl)-6-morpholino-4,5'-bi-pyrimidin-2'-amine, 6-morpholino-$N^2$-(6-(piperazin-1-yl)pyridin-3-yl)-4,5'-bipyrimidine-2,2'-diamine, $N^2$-(6-(4-methylpiperazin-1-yl)pyridin-3-yl)-6-morpholino-4,5'-bi-pyrimidine-2,2'-diamine, 6-morpholino-2-(tetrahydro-2H-pyran-4-yl)-4,5'-bipyrimidin-2'-amine, $N^{2'}$-methyl-$N^2$-(6-(4-methylpiperazin-1-yl)pyridin-3-yl)-6-morpholino-4,5'-bi-pyrimidine-2,2'-diamine, 2-(2H-benzo[b][1,4]oxazin-4(3H)-yl)-N-methyl-6-morpholino-4,5'-bipyrimidin-2'-amine, $N^2$-(6-methoxyquinolin-3-yl)$N^{2'}$-methyl-6-morpholino-4,5'-bipyrimidine-2,2'-diamine, $N^{2'}$-methyl-6-morpholino-$N^2$-(3-(trifluoromethyl)pyridin-4-yl)-4,5'-bipyrimidine-2,2'-diamine, 7-(2'-(methylamino)-6-morpholino-4,5'-bipyrimidin-2-ylamino)-2H-benzo[b][1,4]oxazin-3(4H)-one, $N^{2'}$-methyl-6-morpholino-$N^2$-(8-(trifluoromethyl)quinolin-4-yl)-4,5'-bipyrimidine-2,2'-diamine, and 2-(3,4-di-hydroquinolinyl(2H)-yl)-N-methyl-6-morpholino-4,5'-bipyrimidin-2'-amine or a stereoisomer, tautomer, or a pharmaceutically acceptable salt thereof.

In other aspects, the preferred embodiments provide for methods for manufacture of PI3K inhibitor compounds. It is further contemplated that, in addition to the compounds of Formulas I-III, intermediates, and their corresponding methods of syntheses are included within the scope of the embodiments.

Another embodiment provides a method of inhibiting phosphorylation and activation of Akt comprising administering a compound of Formula I, II, or III to a human in need thereof. Another embodiment provides a method of treating cancer responsive to inhibition of phosphorylation of Akt, comprising administering a compound of Formula I, II, or III. Another embodiment provides a method of inhibiting phosphorylation and activation of Akt comprising contacting a cell with a compound of Formula I, II, or III.

Another embodiment provides for a method for inhibiting phosphorylation of a substrate selected from phosphatidylinositol (PI), phosphatidylinositol phosphate (PIP), or phosphatidylinositol diphosphate ($PIP_2$), comprising exposing said substrate and a lipid kinase thereof to a compound of Formula I, II, or III.

Another embodiment provides a method of inhibiting phosphorylation and activation of Akt comprising orally administering a compound of Formula I, II, or III to a human in need thereof. In a more particular embodiment the human is suffering from cancer. In a more particular embodiment the cancer is responsive to treatment with a compound that inhibits phosphorylation of Akt. In another embodiment the compound is orally bioavailable.

Another embodiment provides a method of treating cancer comprising orally administering a compound of Formula I, II, or III, wherein said compound is capable of inhibiting activity of pAkt.

In some embodiments of the method of inhibiting PI3K, or the catalytic p110α isoform subunit or a variant thereof, using a PI3K inhibitor compound of the embodiments, the $IC_{50}$ value of the compound is less than or equal to about 1 mM with respect to PI3K. In other such embodiments, the $IC_{50}$ value is less than or equal to about 100 μM, is less than or equal to about 25 μM, is less than or equal to about 10 μM, is less than or equal to about 1 μM, is less than or equal to about 0.1 μM, is less than or equal to about 0.050 μM, or is less than or equal to about 0.010 μM.

Some embodiments provide methods of inhibiting phosphorylation and activation of Akt using a compound of the embodiments having an $EC_{50}$ value of less than about 10 μM with respect to inhibition of AKT phosphorylation. In another more particular embodiment, the compound has an $EC_{50}$ value of less than about 1 μM with respect to inhibition of AKT phosphorylation. In a more particular embodiment still, the compound has an $EC_{50}$ value of less than about 0.5 μM with respect to inhibition of AKT phosphorylation. In an even more particular embodiment, the compound has an $EC_{50}$ value of less than about 0.1 μM with respect to inhibition of AKT phosphorylation.

In certain embodiments, a compound is capable of inhibition of phosphorylation of Akt. In certain embodiments, a compound is capable of inhibition of phosphorylation of Akt in a human or animal subject (i.e., in vivo).

In one embodiment, a method of reducing pAKT levels and/or activity in a human or animal subject is provided. In the method, a compound of the preferred embodiments is administered in an amount effective to reduce pAKT levels and/or activity in the human or animal subject (i.e., in vivo).

In some embodiments of the method of inhibiting PI3K, or the catalytic p110α isoform subunit or a variant thereof, using a PI3K inhibitor compound of the embodiments, the $IC_{50}$ value of the compound is between about 1 nM to about 10 nM. In other such embodiments, the $IC_{50}$ value is between about 10 nM to about 50 nM, between about 50 nM to about 100 nM, between about 100 nM to about 1, between about 1 μM to about 25 μM, or is between about 25 μM to about 100 μM.

Another embodiment provides methods of treating a PI3K-mediated disorder. In one method, an effective amount of a PI3K inhibitor compound is administered to a patient (e.g., a human or animal subject) in need thereof to mediate (or modulate) PI3K activity.

The compounds of the preferred embodiment are useful in pharmaceutical compositions for human or veterinary use where inhibition of PI3K is indicated, for example, in the treatment of cellular proliferative diseases such as tumor and/or cancerous cell growth mediated by PI3K. Anti-tumor effect can arise from direct antiproliferative effects due to the inhibition of PI3K combined with antiangiogenic activity that can be obtained upon PI3K inhibition in endothelial cells. In particular, the compounds are useful in the treatment of human or animal (e.g., murine) cancers, including, for example, lung and bronchus; prostate; breast; pancreas; colon and rectum; thyroid; liver and intrahepatic bile duct; hepatocellular; gastric; glioma/glioblastoma; endometrial; melanoma; kidney and renal pelvis; urinary bladder; uterine corpus; uterine cervix; ovary; multiple myeloma; esophagus; acute myelogenous leukemia; chronic myelogenous leukemia; lymphocytic leukemia; myeloid leukemia; brain; oral cavity and pharynx; larynx; small intestine; non-Hodgkin lymphoma; melanoma; and villous colon adenoma.

Agents of the embodiments are also useful in the treatment of inflammatory or obstructive airways diseases, resulting, for example, in reduction of tissue damage, airways inflammation, bronchial hyperreactivity, remodeling or disease progression. Inflammatory or obstructive airways diseases to which the embodiments are applicable include asthma of whatever type of genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics ("wheezy infant syndrome").

Other inflammatory or obstructive airways diseases and conditions to which the embodiments are applicable include acute lung injury (ALI), adult respiratory distress syndrome (ARDS), chronic obstructive pulmonary, airways or lung disease (COPD, COAD or COLD), including pulmonary fibrosis, chronic bronchitis or dyspnea associated therewith, emphysema, as well as exacerbation of airways hyperreactivity consequent to other drug therapy, in particular other inhaled drug therapy. The embodiments are also applicable to the treatment of bronchitis of whatever type or genesis including, e.g., acute, arachidic, catarrhal, croupus, chronic or phthinoid bronchitis. Further inflammatory or obstructive airways diseases to which the embodiments are applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, abestosis, chalicosis, ptilosis, siderosis, silicosis, tabacosis and byssinosis.

Having regard to their anti-inflammatory activity, in particular in relation to inhibition of eosinophil activation, agents of the preferred embodiments are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Agents of the embodiments are also useful in the treatment of inflammatory or allergic conditions of the skin, for example psoriasis, contact dermatitis, atopic dermatitis, alopecia areata, erythema multiforme, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Agents of the embodiments may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune haematogical disorders (e.g. haemolytic anaemia, aplastic anaemia, pure red cell anaemia and idiopathic thrombocytopenia), systemic lupus erythematosus, polychondritis, scleroderma, Wegener granulomatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), interstitial lung fibrosis, psoriatic arthritis and glomerulonephritis (with and without nephritic syndrome, e.g. including idiopathic nephritic syndrome or minal change nephropathy).

Another embodiment provides a method for inhibiting leucocytes, in particular neutrophils and B and T lymphocytes. Exemplary medical conditions that can be treated include those conditions characterized by an undesirable neutrophil function selected from the group consisting of stimulated superoxide release, stimulated exocytosis, and chemotactic migration, preferably without inhibiting phagocytic activity or bacterial killing by the neutrophils.

Another embodiment provides a method for disrupting the function of osteoclasts and ameliorating a bone resorption disorder, such as osteoporosis.

Another embodiment provides treatment of diseases or conditions with agents of the embodiments, such as, but not limited to septic shock, allograft rejection following transplantation, bone disorders such as but not limited to rheumatoid arthritis, ankylosing spondylitis osteoarthritis, obesity, restenosis, diabetes, e.g. diabetes mellitus type I (juvenile diabetes) and diabetes mellitus type II, diarrheal diseases.

In other embodiments, the PI3K-mediated condition or disorder is selected from the group consisting of: cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease, reperfusion injuries, retinopathy, such as diabetic retinopathy or hyperbaric oxygen-induced retinopathy, and conditions characterized by elevated intraocular pressure or secretion of ocular aqueous humor, such as glaucoma.

As described above, since PI3K serves as a second messenger node that integrates parallel signaling pathways, evidence is emerging that the combination of a PI3K inhibitor with inhibitors of other pathways will be useful in treating cancer and proliferative diseases in humans.

Approximately 20-30% of human breast cancers overexpress Her-2/neu-ErbB2, the target for the drug trastuzumab. Although trastuzumab has demonstrated durable responses in some patients expressing Her2/neu-ErbB2, only a subset of these patients respond. Recent work has indicated that this limited response rate can be substantially improved by the combination of trastuzumab with inhibitors of PI3K or the PI3K/AKT pathway (Chan et al., *Breast Can. Res. Treat.* 91:187 (2005), Woods Ignatoski et al., *Brit. J. Cancer* 82:666 (2000), Nagata et al., *Cancer Cell* 6:117 (2004)).

A variety of human malignancies express activating mutations or increased levels of Her1/EGFR and a number of antibody and small molecule inhibitors have been developed against this receptor tyrosine kinase including tarceva, gefitinib and erbitux. However, while EGFR inhibitors demonstrate anti-tumor activity in certain human tumors (e.g., NSCLC), they fail to increase overall patient survival in all patients with EGFR-expressing tumors. This may be rationalized by the fact that many downstream targets of Her1/EGFR are mutated or deregulated at high frequencies in a variety of malignancies, including the PI3K/Akt pathway. For example, gefitinib inhibits the growth of an adenocarcinoma cell line in in vitro assays. Nonetheless, sub-clones of these cell lines can be selected that are resistant to gefitinib that demonstrate increased activation of the PI3/Akt pathway. Down-regulation or inhibition of this pathway renders the resistant sub-clones sensitive to gefitinib (Kokubo et al., *Brit. J. Cancer* 92:1711 (2005)). Furthermore, in an in vitro model of breast cancer with a cell line that harbors a PTEN mutation and over-expresses EGFR inhibition of both the PI3K/Akt pathway and EGFR produced a synergistic effect (She et al., *Cancer Cell* 8:287-297 (2005)). These and additional results indicate that combinations of one or more modulators of the EGFR family of receptor tyrosine kinases and a PI3K/Akt pathway inhibitor of the present invention are useful in the treatment of cancer.

In addition, the TSC2 protein (also called tuberin), has recently been identified as an Akt substrate. TSC2 is a tumor suppressor that forms a heterodimeric complex with the TSC1 protein (also called hamartin). Mutations in TSC1 or TSC2 give rise to the tuberous sclerosis complex (TSC). The TSC1-2 complex negatively regulates the mammalian target of rapamycin (mTOR)-raptor complex (mTORC1). TSC2 is a GTPase-activating protein (GAP) for the Ras-related small G protein Rheb, which activates mTORC1 kinase activity when in its GTP-bound active form. Sarbassov et al., *Curr Opin Cell Biol.* 17:596-603 (2005). mTOR activation is downstream of PI3K-Akt signaling in this pathway, and reciprocally regulates the growth-factor responsiveness of PI3K and Akt. When mTOR is associated with rictor in the mTOR complex 2 (mTORC2), it directly phosphorylates Akt, thereby contributing to Akt activation. Sarbassov et al., *Science.* 307:1098-1101 (2005). Accordingly, the combination of one or more modulators of mTORC1 and a PI3K/Akt pathway inhibitor of the present invention are useful in the treatment of cancer.

Anti-estrogens, such as tamoxifen, inhibit breast cancer growth through induction of cell cycle arrest that requires the action of the cell cycle inhibitor p27Kip. Recently, it has been shown that activation of the Ras-Raf-MAP Kinase pathway alters the phosphorylation status of p27Kip such that its inhibitory activity in arresting the cell cycle is attenuated, thereby contributing to anti-estrogen resistance (Donovan, et al, *J. Biol. Chem.* 276:40888, (2001)). As reported by Donovan et al., inhibition of MAPK signaling through treatment with MEK inhibitor reversed the aberrant phosphorylation status of p27 in hormone refractory breast cancer cell lines and in so doing restored hormone sensitivity. Similarly, phosphorylation of p27Kip by Akt also abrogates its role to arrest the cell cycle (Viglietto et al., *Nat. Med.* 8:1145 (2002)). Accordingly, in one aspect, the compounds of Formulas I-III may be used in the treatment of hormone dependent cancers, such as breast and prostate cancers, to reverse hormone resistance commonly seen in these cancers with conventional anticancer agents.

In hematological cancers, such as chronic myelogenous leukemia (CML), chromosomal translocation is responsible for the constitutively activated BCR-Abl tyrosine kinase. The afflicted patients are responsive to imatinib, a small molecule tyrosine kinase inhibitor, as a result of inhibition of Abl kinase activity. However, many patients with advanced stage disease respond to imatinib initially, but then relapse later due to resistance-conferring mutations in the Abl kinase domain. In vitro studies have demonstrated that BCR-Abl employs the Ras-Raf kinase pathway to elicit its effects. In addition, inhibiting more than one kinase in the same pathway provides additional protection against resistance-conferring mutations. Accordingly, in another aspect of the embodiments, the compounds of Formulas I-III are used in combination with at least one additional agent, such as Gleevec®, nilotinib or dasatinib in the treatment of hematological cancers, such as chronic myelogenous leukemia (CML), to reverse or prevent resistance to at least one additional agent.

Other aspects of the invention relate to the treatment of acute myelogenous leukemia (AML). AML is an aggressive cancer and represents 90% of all adult acute leukemias with an incidence of 3.9 per 100,000 and an estimated 10,500 new cases each year. Redaelli, A. et al., *Exper. Rev. Anticancer. Ther.,* 3:695-710 (2003). Cytotoxic agents (AraC+anthracycline) can induce remission in up to 70% of AML patients. However, a large fraction relapse reflecting the need for more effective therapies. Weick, J. K. et al., *Blood,* 88:2841-2851 (1996); Vogler, W. R. et al., *J. Clin. Oncol.,* 10:1103-1111 (1992). Tumor-cell genotyping indicates 25-35% of AML blasts carry fms-like tyrosine kinase (flt3/Flk2/Stk-2) mutations, whereas a larger fraction (>70%) express wild-type FLT3. Gilliland, D. G. et al., *Curr. Opin. Hematol.,* 9:274-281 (2002); Nakao, M. et al., *Leukemia,* 10:1911-1918 (1996); Yokota, S. et al., *Leukemia,* 11:1605-1609 (1997). FLT3 receptor is a member of Class III receptor tyrosine kinases (RTK) that includes CSF-1R, c-KIT, PDGFR, and are functionally known to play an important role in proliferation, differentiation, and survival of hematopoietic cells, dendritic cells, natural killer (NK) cells and progenitor B cells. McKenna, H. J. et al. *Blood,* 95:3489-3497 (2000); Mackarehtschian, K. et al., Immunity, 3:147-161 (1995). FLT3, like other RTKs, is characterized by five IG-like extracellular domains and contains a hydrophilic kinase insert domain. Blume- Jensen, P. et al., *Nature*, 411:355-365 (2001). Signal transduction following ligation of FLT3 modulates multiple downstream pathways, including STAT5 (signal transducer and activator of transcription 5), Ras/MAPK (mitogen-activated protein kinase), and PI3K. Hayakawa, F. et al., *Oncogene*, 19:624-631 (2000); Takahashi, S. et al., Biochem. Biophys. Res. Commun., 316:85-92 (2004); Zhang, S. et al., J. Exp. Med., 192:719-728 (2000); Rosnet, O. et al., *Acta Haematol.*, 95:218-223 (1996). In cells with mutant FLT3, oncogenic signaling has been linked to constitutive kinase activation (in the absence of FLT3 ligation) arising from dysregulated kinase activation and/or loss of function of the autoinhibitory domain. Stirewalt, D. L. et al., *Nat. Rev. Cancer*, 3:650-665 (2003); Brown, P. et al., *Eur. J. Cancer*, 40:707-721 (2004). Molecular characterization of these FLT3 mutations have revealed either internal tandem duplications (ITD) in the juxtamembrane region of FLT3 or point mutations in the kinase domain (ASP835/836), with 17-34% being FLT3 ITD and approximately 7% point mutations. Yamamoto, Y. et al., *Blood*, 97:2434-2439 (2001); Thiede, C., et al., Blood, 99:43264335 (2002); Abu-Duhier, F. M. et al., Br. *J. Haematol.*, 113:983-988 (2001). Furthermore, there is considerable evidence that implicate FLT3 ITD mutations as a negative prognostic in AML, correlating with increased disease relapse, and decreased overall survival. Thiede, C. et al., *Blood*, 99:4326-4335 (2002); Schnittger, S. et al., Blood, 100: 59-66 (2002). Given the relevance of FLT3 mutations in AML, a number of targeted approaches utilizing small molecules kinase inhibitors/antibodies to FLT3 are being currently explored in preclinical or early phases of drug development. Brown, P. et al., *Eur. J. Cancer*, 40:707-721 (2004); O'Farrell, A. M. et al., *Clin. Cancer Res.,* 9:5464-5476 (2003); Weisberg, E., et al., *Cancer Cell*, 1:433-443 (2002); Smith, B. D. et al., *Blood*, (2004); Kelly, L. M. et al., *Cancer Cell*, 1:421-432 (2002). Accordingly, in another aspect of the embodiments, the compounds of Formulas I-III are used either alone or in combination with at least one additional agent, such as PKC412 or TKI258 in the treatment of hematological cancers, such as acute myelogenous leukemia (AML).

Because activation of the PI3K/Akt pathway drives cell survival, inhibition of the pathway in combination with therapies that drive apoptosis in cancer cells, including radiotherapy and chemotherapy, will result in improved responses (Ghobrial et al., CA *Cancer J. Clin* 55:178-194 (2005)). As an example, combination of PI3 kinase inhibitor with carboplatin demonstrated synergistic effects in both in vitro proliferation and apoptosis assays as well as in in vivo tumor efficacy in a xenograft model of ovarian cancer (Westfall and Skinner, *Mol. Cancer. Ther.* 4:1764-1771 (2005)).

In addition to cancer and proliferative diseases, there is accumulating evidence that inhibitors of Class 1A and 1B PI3 kinases would be therapeutically useful in others disease areas. The inhibition of p110β, the PI3K isoform product of the PIK3CB gene, has been shown to be involved in shear-induced platelet activation (Jackson et al., *Nature Medicine* 11:507-514 (2005)). Thus, a PI3K inhibitor that inhibits p110β would be useful as a single agent or in combination in anti-thrombotic therapy. The isoform p110β, the product of the PIK3CD gene, is important in B cell function and differentiation (Clayton et al., *J. Exp. Med.* 196:753-763 (2002)), T-cell dependent and independent antigen responses (Jou et al., *Mol. Cell. Biol.* 22:8580-8590 (2002)) and mast cell differentiation (Ali et al., *Nature* 431:1007-1011 (2004)). Thus, it is expected that p110β-inhibitors would be useful in the treatment of B-cell driven autoimmune diseases and asthma. Finally, the inhibition of p110β, the isoform product of the PI3KCG gene, results in reduced T, but not B cell, response (Reif et al., *J. Immunol.* 173:2236-2240 (2004)) and its inhibition demonstrates efficacy in animal models of autoimmune diseases (Camps et al., *Nature Medicine* 11:936-943 (2005), Barber et al., *Nature Medicine* 11:933-935 (2005)).

The preferred embodiments provide pharmaceutical compositions comprising at least one compound of Formula I, II, or III together with a pharmaceutically acceptable carrier suitable for administration to a human or animal subject, either alone or together with other anticancer agents.

Another embodiment provides methods of treating human or animal subjects suffering from a cellular proliferative disease, such as cancer. The preferred embodiments provide methods of treating a human or animal subject in need of such treatment, comprising administering to the subject a therapeutically effective amount of a compound of Formula I, II, or III, either alone or in combination with other anticancer agents.

In particular, compositions will either be formulated together as a combination therapeutic or administered separately. Anticancer agents for use with the preferred embodiments include, but are not limited to, one or more of the following set forth below:

A. Kinase Inhibitors

Kinase inhibitors for use as anticancer agents in conjunction with the compositions of the preferred embodiments include inhibitors of the Ras/Raf/MEK/ERK pathway, including RAF265 (Novartis); inhibitors of Epidermal Growth Factor Receptor (EGFR) kinases such as small molecule quinazolines, for example gefitinib (U.S. Pat. Nos. 5,457,105, 5,616,582, and 5,770,599), ZD-6474 (WO 01/32651), erlotinib (Tarceva®, U.S. Pat. No. 5,747,498 and WO 96/30347), and lapatinib (U.S. Pat. No. 6,727,256 and WO 02/02552); Vascular Endothelial Growth Factor Receptor (VEGFR) kinase inhibitors, including SU-11248 (WO 01/60814), SU 5416 (U.S. Pat. No. 5,883,113 and WO 99/61422), SU 6668 (U.S. Pat. No. 5,883,113 and WO 99/61422), CHIR-258 (U.S. Pat. Nos. 6,605,617 and 6,774,237), vatalanib or PTK-787 (U.S. Pat. No. 6,258,812), VEGF-Trap (WO 02/57423), B43-Genistein (WO-09606116), fenretinide (retinoic acid p-hydroxyphenylamine) (U.S. Pat. No. 4,323,581), IM-862 (WO 02/62826), bevacizumab or Avastin® (WO 94/10202), KRN-951, 3-[5-(methylsulfonylpiperadine methyl)indolyl]-quinolone, AG-13736 and AG-13925, pyrrolo[2,1-f][1,2,4]triazines, ZK-304709, Veglin®, VMDA-3601, EG-004, CEP-701 (U.S. Pat. No. 5,621,100), Cand5 (WO 04/09769); Erb2 tyrosine kinase inhibitors such as pertuzumab (WO 01/00245), trastuzumab, and rituximab; Akt protein kinase inhibitors, such as RX-0201; Protein Kinase C (PKC) inhibitors, such as LY-317615 (WO 95/17182), and perifosine (US 2003171303); Raf/Map/MEK/Ras kinase inhibitors including sorafenib (BAY 43-9006), ARQ-350RP, LErafAON, BMS-354825 AMG-548, and others disclosed in WO 03/82272; Fibroblast Growth Factor Receptor (FGFR) kinase inhibitors; Cell Dependent Kinase (CDK) inhibitors, including CYC-202 or roscovitine (WO 97/20842 and WO 99/02162); Platelet-Derived Growth Factor Receptor (PDGFR) kinase inhibitors such as TKI258, 3G3 mAb, AG-13736, SU-11248 and SU6668; and Bcr-Abl kinase inhibitors and fusion proteins such as STI-571 or Gleevec® (imatinib).

B. Anti-Estrogens

Estrogen-targeting agents for use in anticancer therapy in conjunction with the compositions of the preferred embodiments include Selective Estrogen Receptor Modulators (SERMs) including tamoxifen, toremifene, and raloxifene;

aromatase inhibitors, including anastrozole (Arimidex®) and letrozole (Femara®); and Estrogen Receptor Downregulators (ERDs), including fulvestrant (Faslodex®).

C. Anti-Androgens

Androgen-targeting agents for use in anticancer therapy in conjunction with the compositions of the preferred embodiments include flutamide, bicalutamide, finasteride, aminoglutethamide, ketoconazole, and corticosteroids.

D. Other Inhibitors

Other inhibitors for use as anticancer agents in conjunction with the compositions of the preferred embodiments include protein farnesyl transferase inhibitors including tipifarnib or R-115777 (US 2003134846 and WO 97/21701), BMS-214662, AZD-3409, and FTI-277; topoisomerase inhibitors including merbarone and diflomotecan (BN-80915); mitotic kinesin spindle protein (KSP) inhibitors including SB-743921 and MKI-833; proteasome modulators such as bortezomib or Velcade® (U.S. Pat. No. 5,780,454), XL-784; HSP90 modulators including AUY922; and cyclooxygenase 2 (COX-2) inhibitors including non-steroidal antiinflammatory drugs I (NSAIDs).

E. Cancer Chemotherapeutic Drugs

Particular cancer chemotherapeutic agents for use as anticancer agents in conjunction with the compositions of the preferred embodiments include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®, US 2004073044), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

F. Alkylating Agents

Alkylating agents for use in conjunction with the compositions of the preferred embodiments for anticancer therapeutics include VNP-40101M or cloretizine, oxaliplatin (U.S. Pat. No. 4,169,846, WO 03/24978 and WO 03/04505), glufosfamide, mafosfamide, etopophos (U.S. Pat. No. 5,041,424), prednimustine; treosulfan; busulfan; irofluven (acylfulvene); penclomedine; pyrazoloacridine (PD-115934); O6-benzylguanine; decitabine (5-aza-2-deoxycytidine); brostallicin; mitomycin C (MitoExtra); TLK-286 (Telcyta®); temozolomide; trabectedin (U.S. Pat. No. 5,478,932); AP-5280 (Platinate formulation of Cisplatin); porfiromycin; and clearazide (meclorethamine).

G. Chelating Agents

Chelating agents for use in conjunction with the compositions of the preferred embodiments for anticancer therapeutics include tetrathiomolybdate (WO 01/60814); RP-697; Chimeric T84.66 (cT84.66); gadofosveset (Vasovist®); deferoxamine; and bleomycin optionally in combination with electorporation (EPT).

H. Biological Response Modifiers

Biological response modifiers, such as immune modulators, for use in conjunction with the compositions of the preferred embodiments for anticancer therapeutics include staurosprine and macrocyclic analogs thereof, including UCN-01, CEP-701 and midostaurin (see WO 02/30941, WO 97/07081, WO 89/07105, U.S. Pat. No. 5,621,100, WO 93/07153, WO 01/04125, WO 02/30941, WO 93/08809, WO 94/06799, WO 00/27422, WO 96/13506 and WO 88/07045); squalamine (WO 01/79255); DA-9601 (WO 98/04541 and U.S. Pat. No. 6,025,387); alemtuzumab; interferons (e.g. IFN-a, IFN-b etc.); interleukins, specifically IL-2 or aldesleukin as well as IL-1, IL-3, IL-4, IL-5, IL-6, IL-7, IL-8, IL-9, IL-10, IL-11, IL-12, and active biological variants thereof having amino acid sequences greater than 70% of the native human sequence; altretamine (Hexylen®); SU 101 or leflunomide (WO 04/06834 and U.S. Pat. No. 6,331,555); imidazoquinolines such as resiquimod and imiquimod (U.S. Pat. Nos. 4,689,338, 5,389,640, 5,268,376, 4,929,624, 5,266, 575, 5,352,784, 5,494,916, 5,482,936, 5,346,905, 5,395,937, 5,238,944, and 5,525,612); and SMIPs, including benzazoles, anthraquinones, thiosemicarbazones, and tryptanthrins (WO 04/87153, WO 04/64759, and WO 04/60308).

I. Cancer Vaccines:

Anticancer vaccines for use in conjunction with the compositions of the preferred embodiments include Avicine® (*Tetrahedron Lett.* 26:2269-70 (1974)); oregovomab (OvaRex®); Theratope®& (STn-KLH); Melanoma Vaccines; GI-4000 series (GI-4014, GI-4015, and GI-4016), which are directed to five mutations in the Ras protein; Glio-Vax-1; MelaVax; Advexin® & or INGN-201 (WO 95/12660); Sig/E7/LAMP-1, encoding HPV-16 E7; MAGE-3 Vaccine or M3TK (WO 94/05304); HER-2VAX; ACTIVE, which stimulates T-cells specific for tumors; GM-CSF cancer vaccine; and *Listeria monocytogenes*-based vaccines.

J. Antisense Therapy:

Anticancer agents for use in conjunction with the compositions of the preferred embodiments also include antisense compositions, such as AEG-35156 (GEM-640); AP-12009 and AP-11014 (TGF-beta2-specific antisense oligonucleotides); AVI-4126; AVI4557; AVI-4472; oblimersen (Genasense®); JFS2; aprinocarsen (WO 97/29780); GTI-2040 (R2 ribonucleotide reductase mRNA antisense oligo) (WO 98/05769); GTI-2501 (WO 98/05769); liposome-encapsulated c-Raf antisense oligodeoxynucleotides (LErafAON) (WO 98/43095); and Sima-027 (RNAi-based therapeutic targeting VEGFR-1 mRNA).

The compounds of the preferred embodiments can also be combined in a pharmaceutical composition with bronchiodilatory or antihistamine drugs substances. Such bronchiodilatory drugs include anticholinergic or antimuscarinic agents, in particular ipratropium bromide, oxitropium bromide, and tiotropium bromide, and β-2-adrenoreceptor agonists such as salbutamol, terbutaline, salmeterol and, especially, formoterol. Co-therapeutic antihistamine drug substances include cetirizine hydrochloride, clemastine fumarate, promethazine, loratadine, desloratadine diphenhydramine and fexofenadine hydrochloride.

The compounds of the preferred embodiments can also be combined in a pharmaceutical composition with compounds that are useful for the treatment of a thrombolytic disease, heart disease, stroke, etc., (e.g., aspirin, streptokinase, tissue plasminogen activator, urokinase, anticoagulants, antiplatelet drugs (e.g, PLAVIX; clopidogrel bisulfate), a statin (e.g., LIPITOR or Atorvastatin calcium), ZOCOR (Simvastatin), CRESTOR (Rosuvastatin), etc.), a Beta blocker (e.g., Atenolol), NORVASC (amlodipine besylate), and an ACE inhibitor (e.g., lisinopril).

The compounds of the preferred embodiments can also be combined in a pharmaceutical composition with compounds that are useful for the treatment of antihypertension agents such as, ACE inhibitors, lipid lowering agents such as statins, LIPITOR (Atorvastatin calcium), calcium channel blockers dush as NORVASC (amlodipine besylate). The compounds of the preferred embodiments may also be used in combination with fibrates, beta-blockers, NEPI inhibitors, Angiotensin-2 receptor antagonists and platelet aggregation inhibitors.

For the treatment of inflammatory diseases, including rheumatoid arthritis, the compounds of the preferred embodiments may be combined with agents such as TNF-α inhibitors such as anti-TNF-α monoclonal antibodies (such as REMICADE, CDP-870) and D2E7 (HUMIRA) and TNF receptor immunoglobulin fusion molecules (such as ENBREL), IL-1 inhibitors, receptor antagonists or soluble IL-1Rα(e.g. KINERET or ICE inhibitors), nonsterodial anti-inflammatory agents (NSAIDS), piroxicam, diclofenac, naproxen, flurbiprofen, fenoprofen, ketoprofen ibuprofen, fenamates, mefenamic acid, indomethacin, sulindac, apazone, pyrazolones, phenylbutazone, aspirin, COX-2 inhibitors (such as CELEBREX (celecoxib), PREXIGE (lumiracoxib)), metalloprotease inhibitors (preferably MMP-13 selective inhibitors), p2×7 inhibitors, α2αinhibitors, NEUROTIN, pregabalin, low dose methotrexate, leflunomide, hydroxyxchloroquine, d-penicillamine, auranofin or parenteral or oral gold.

The compounds of the preferred embodiments can also be used in combination with the existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flurbiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, lumiracoxib and etoricoxib, analgesics and intraarticular therapies such as corticosteroids and hyaluronic acids such as hyalgan and synvisc.

The compounds of the preferred embodiments may also be used in combination with antiviral agents such as Viracept, AZT, acyclovir and famciclovir, and antisepsis compounds such as Valant.

The compounds of the preferred embodiments may also be used in combination with CNS agents such as antidepressants (sertraline), anti-Parkinsonian drugs (such as deprenyl, L-dopa, Requip, Mirapex, MAOB inhibitors such as selegine and rasagiline, comP inhibitors, such as Tasmar, A-2 inhibitors, dopamine reuptake inhibitors, NMDA antagonists, Nicotine agonists, Dopamine agonists, and inhibitors of neuronal nitric oxide synthase), and anti-Alzheimer's drugs such as donepezil, tacrine, α2δinhibitors, NEUROTIN, pregabalin, COX-2 inhibitors, propentofylline or metryfonate.

The compounds of the preferred embodiments may also be used in combination with osteoporosis agents such as EVISTA (raloxifene hydrochloride), droloxifene, lasofoxifene or fosomax and immunosuppressant agents such as FK-506 and rapamycin.

In another aspect of the preferred embodiments, kits that include one or more compounds of the preferred embodiments are provided. Representative kits include a PI3K inhibitor compound of the preferred embodiments (e.g., a compound of Formula I, II, or III) and a package insert or other labeling including directions for treating a cellular proliferative disease by administering a PI3K inhibitory amount of the compound.

Administration and Pharmaceutical Composition

In general, the compounds of preferred embodiments will be administered in a therapeutically effective amount by any of the accepted modes of administration for agents that serve similar utilities. The actual amount of the compound of preferred embodiments, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day. All of these factors are within the skill of the attending clinician.

Therapeutically effective amounts of compounds of Formulas I-III may range from about 0.05 to about 50 mg per kilogram body weight of the recipient per day; preferably about 0.1-25 mg/kg/day, more preferably from about 0.5 to 10 mg/kg/day. Thus, for administration to a 70 kg person, the dosage range would most preferably be about 35-70 mg per day.

In general, compounds of the preferred embodiments will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of the preferred embodiments is inhalation. This is an effective method for delivering a therapeutic agent directly to the respiratory tract (see U.S. Pat. No. 5,607,915).

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory airstream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula I, II, or III in combination with at least one pharmaceutically acceptable excipient. Acceptable excipients are non-toxic, aid administration, and do not adversely affect the therapeutic benefit of the compound of Formula I, II, or III. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of the preferred embodiments in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01-99.99 wt % of a compound of Formula I, II, or III based on the total formulation, with the balance being one or more suitable pharmaceutical excipients. Preferably, the compound is present at a level of about 1-80 wt %.

General Synthetic Methods

The compounds of the invention can be obtained through procedures known to the skilled in the art. For example a halogenated pyrimidinyl compound such as 2,4-dichloro-6-morpholinopyrimidine 1 (Scheme 1) can be reacted with suitable oxygen, nitrogen or sulfur nucleophiles to obtain the two regioisomeric intermediates 2 and 3. Compounds 2 and 3 can be separated through suitable separation techniques known to the skilled in the art such as, for example chromatography, preparative HPLC or recrystallization. Subsequent Suzuki reaction of 2 with suitable boronic acids or esters, affords the desired compound 4 as shown in scheme 1.

Scheme 1:

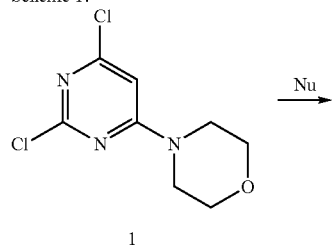

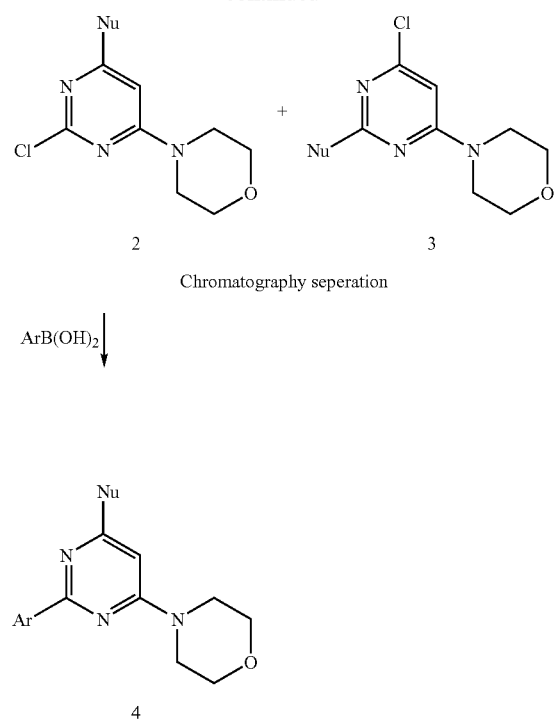

As an alternative, commercially available 2,4,6-trichloropyrimidine can be used as starting material. Nucleophilic aromatic substitution with suitable nucleophiles or reaction with aromatic amines using Buchwald conditions results in 6-substituted 2,4-dichloropyrimidine intermediate 6 (Scheme 2). Reaction with morpholine under nucleophilic aromatic substitution conditions leads to the formation of two regioisomeric intermediates. The desired intermediate 7 can be isolated using the methods described above. Subsequent coupling with suitable boronic acids or esters under Suzuki conditions affords the desired product 8.

Scheme 2:

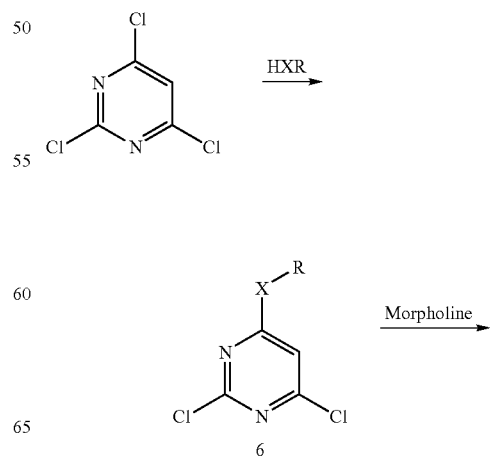

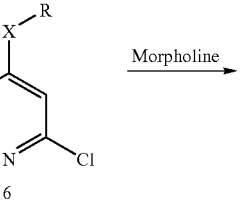

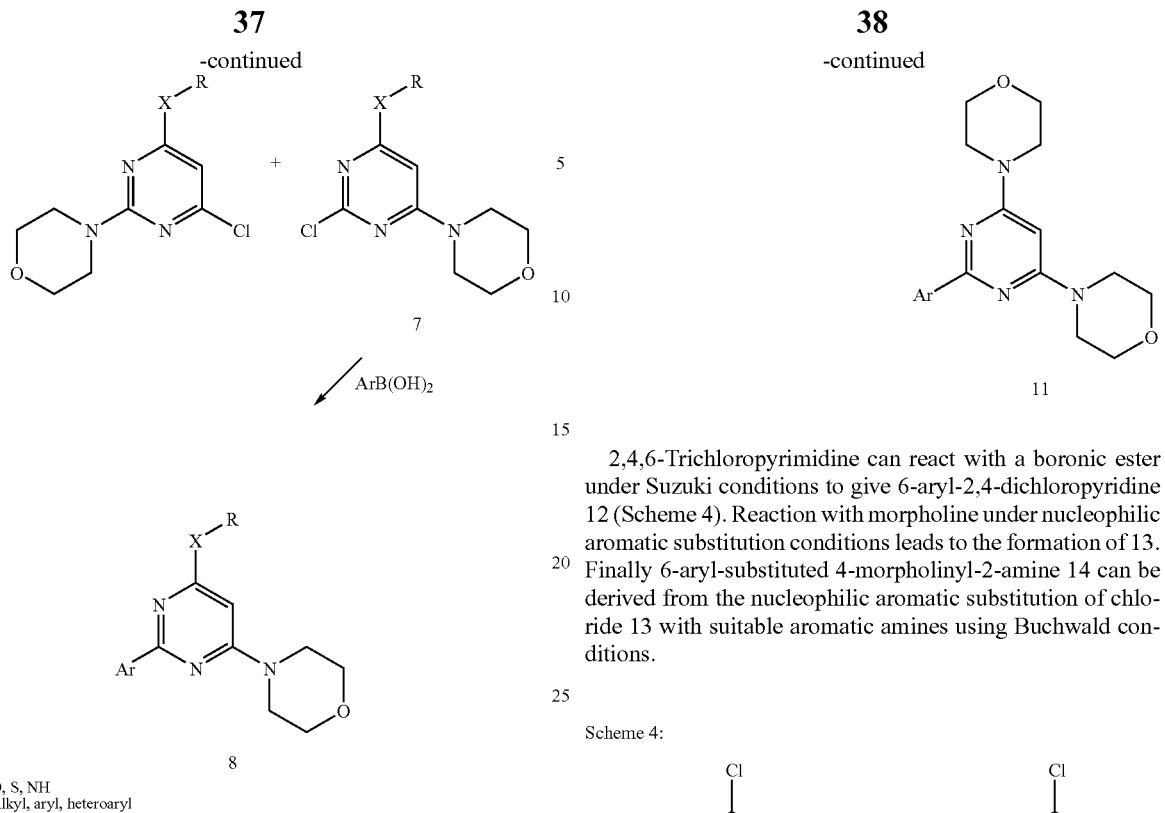

X = O, S, NH
R = Alkyl, aryl, heteroaryl

As an additional alternative, 2,4,6-trichloropyrimidine can be reacted with nucleophiles such as, for example morpholine, under forcing conditions to obtain the disubstituted chloropyrimidines shown in Scheme 3. Again, the two regioisomers 9 and 10 can be separated and 10 subjected to Suzuki coupling with suitable boronic acids and esters to afford the desired product 11

Scheme 3:

2,4,6-Trichloropyrimidine can react with a boronic ester under Suzuki conditions to give 6-aryl-2,4-dichloropyridine 12 (Scheme 4). Reaction with morpholine under nucleophilic aromatic substitution conditions leads to the formation of 13. Finally 6-aryl-substituted 4-morpholinyl-2-amine 14 can be derived from the nucleophilic aromatic substitution of chloride 13 with suitable aromatic amines using Buchwald conditions.

Scheme 4:

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

Furthermore, the compounds of preferred embodiments contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of the preferred embodiments, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chem or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley and Sons, 1991), Rodd's *Chemistry of Carbon Compounds*, Volumes 1-5 and Supplementals (Elsevier Science Publishers, 1989), *Organic Reactions*, Volumes 1-40 (John Wiley and Sons, 1991), March's *Advanced Organic Chemistry*, (John Wiley and Sons, 4$^{th}$ Edition), and Larock's *Comprehensive Organic Transformations* (VCH Publishers Inc., 1989).

The various starting materials, intermediates, and compounds of the preferred embodiments may be isolated and purified where appropriate using conventional techniques such as precipitation, filtration, crystallization, evaporation, distillation, and chromatography. Characterization of these compounds may be performed using conventional methods such as by melting point, mass spectrum, nuclear magnetic resonance, and various other spectroscopic analyses.

Compounds of preferred embodiments can be made by employing palladium mediated coupling reactions, such as Suzuki coupling. Said couplings can be employed to functionalize a heterocycle or aryl ring system at each position of the ring system providing said ring is suitably activated or functionalized.

Suzuki coupling (Suzuki et al., *Chem. Commun.* (1979) 866) can be used to form the final product and can be effected under known conditions such as by treatment with functionalized boronic esters as in the following schemes:

More particular syntheses of compounds of the preferred embodiments, particularly those of Formulas I, II, and III, are provided in the following Methods and Examples:

EXAMPLES

Referring to the examples that follow, compounds of the preferred embodiments were synthesized using the methods described herein, or other methods, which are known in the art.

The compounds and/or intermediates were characterized by high performance liquid chromatography (HPLC) using a Waters Millenium chromatography system with a 2695 Separation Module (Milford, Mass.). The analytical columns were reversed phase Phenomenex Luna C18-5µ, 4.6×50 mm, from Alltech (Deerfield, Ill.). A gradient elution was used (flow 2.5 mL/min), typically starting with 5% acetonitrile/95% water and progressing to 100% acetonitrile over a period of 10 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.).

In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well-known iodine vapor and other various staining techniques.

Mass spectrometric analysis was performed on one of two LCMS instruments: a Waters System (Alliance HT HPLC and a Micromass ZQ mass spectrometer; Column: Eclipse XDB-C18, 2.1×50 mm; gradient: 5-95% (or 35-95%, or 65-95% or 95-95%) acetonitrile in water with 0.05% TFA over a 4 min period; flow rate 0.8 mL/min; molecular weight range 200-1500; cone Voltage 20 V; column temperature 40° C.) or a Hewlett Packard System (Series 1100 HPLC; Column: Eclipse XDB-C18, 2.1×50 mm; gradient: 5-95% acetonitrile in water with 0.05% TFA over a 4 min period; flow rate 0.8 mL/min; molecular weight range 150-850; cone Voltage 50 V; column temperature 30° C.). All masses were reported as those of the protonated parent ions.

GCMS analysis is performed on a Hewlett Packard instrument (HP6890 Series gas chromatograph with a Mass Selective Detector 5973; injector volume: 1 µL; initial column temperature: 50° C.; final column temperature: 250° C.; ramp time: 20 minutes; gas flow rate: 1 mL/min; column: 5% phenyl methyl siloxane, Model No. HP 190915-443, dimensions: 30.0 m×25 m×0.25 m).

Nuclear magnetic resonance (NMR) analysis was performed on some of the compounds with a Varian 300 MHz NMR (Palo Alto, Calif.). The spectral reference was either TMS or the known chemical shift of the solvent. Some compound samples were run at elevated temperatures (e.g., 75° C.) to promote increased sample solubility.

The purity of some of the compounds is assessed by elemental analysis (Desert Analytics, Tucson, Ariz.).

Melting points are determined on a Laboratory Devices MeI-Temp apparatus (Holliston, Mass.).

Preparative separations are carried out using a Flash 40 chromatography system and KP-Sil, 60A (Biotage, Charlottesville, Va.), or by flash column chromatography using silica gel (230-400 mesh) packing material, or by HPLC using a Waters 2767 Sample Manager, C-18 reversed phase column, 30×50 mm, flow 75 mL/min. Typical solvents employed for the Flash 40 Biotage system and flash column chromatography are dichloromethane, methanol, ethyl acetate, hexane, acetone, aqueous ammonia (or ammonium hydroxide), and triethyl amine. Typical solvents employed for the reverse phase HPLC are varying concentrations of acetonitrile and water with 0.1% trifluoroacetic acid.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

It is understood that the invention is not limited to the embodiments set forth herein for illustration, but embraces all such forms thereof as come within the scope of the above disclosure.

The examples below as well as throughout the application, the following abbreviations have the following meanings. If not defined, the terms have their generally accepted meanings.

| ABBREVIATIONS | |
|---|---|
| ACN | acetonitrile |
| DCM | dichloromethane |

-continued

| ABBREVIATIONS | |
|---|---|
| DIEA | diisopropylethylamine |
| DME | 1,2-dimethoxyethane |
| DMF | N,N-dimethylformamide |
| dppf | 1,1'-bis(diphenylphosphino)ferrocene |
| EtOAc | ethyl acetate |
| EtOH | ethanol |
| MeOH | methanol |
| NaHCO$_3$ | sodium bicarbonate |
| NBS | N-bromosuccinimide |
| NMP | N-methyl-2-pyrrolidone |
| RT or rt | room temperature |
| THF | tetrahydrofuran |

The following methods were used for compounds of Formula I, II, or III:

Method 1

Preparation of 2,4-dimorpholino-6-chloropyrimidine

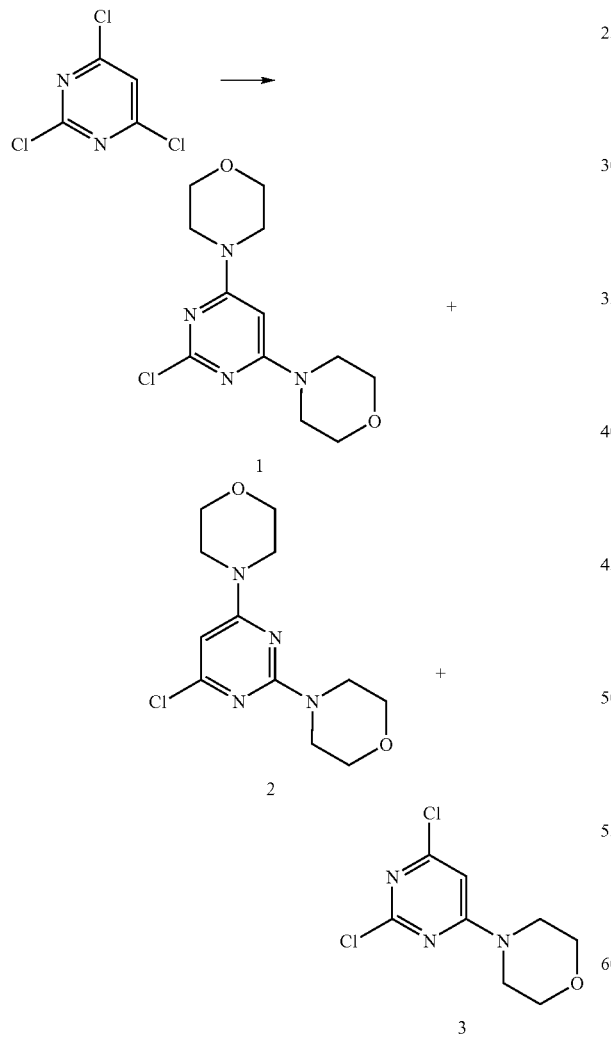

To a dry round bottom flask was added 2,4,6-trichloropyrimidine (5 g, 27 mmol) and EtOH (200 mL), followed by DIEA (16 mL, 82 mmol) at 0° C. Morpholine (5.6 g, 68 mmol) was added slowly at 0° C. The reaction was slowly warmed up to room temperature and stirred overnight. LC and LCMS indicated that a mixture (7:1) of 2,4-dimorpholino-6-chloropyrimidine 2 and 4,6-dimorpholino-2-chloropyrimidine 1 were formed. Formation of 2,6-dichloro-4-morpholinopyrimidine 3 was also observed. Water (700 mL) was added to the reaction mixture was and the resulting precipitate was filtered to give 7 g of the mixture described above. The crude material was purified by silica gel chromatography (3%-20% EtOAc-DCM) yielding 4,6-dimorpholino-2-chloropyrimidine (1, 500 mg, 6%); 2,4-dimorpholino-6-chloropyrimidine (2, 4.6 g, 59%) and 2,6-dichloro-4-morpholinopyrimidine (3, 1.5 g, 24%).

4,6-dimorpholino-2-chloropyrimidine 1: LCMS (m/z): 284.8 (MH$^+$); $^1$H NMR (CDCl$_3$): δ 5.4 (s, 1H), 3.76 (q, 8H), 3.55 (q, 8H).

2,4-dimorpholino-6-chloropyrimidine 2: LCMS (m/z): 284.8 (MH$^+$); $^1$H NMR (CDCl$_3$): δ 5.88 (s, 1H), 3.74 (m, 12H), 3.55 (q, 4H).

2,4-dicholoro-6-morpholinopyrimidine 3: LCMS (m/z): 233.8 (MH$^+$); $^1$H NMR (CDCl$_3$): δ 6.4 (s, 1H), 3.77 (m, 4H), 3.65 (bs, 4H).

Method 2

Preparation of 4-chloro-6-morpholino-2-(tetrahydro-2H-pyran-4-yloxy)pyrimidine and 2-chloro-4-morpholino-6-(tetrahydro-2H-pyran-4-yloxy)pyrimidine

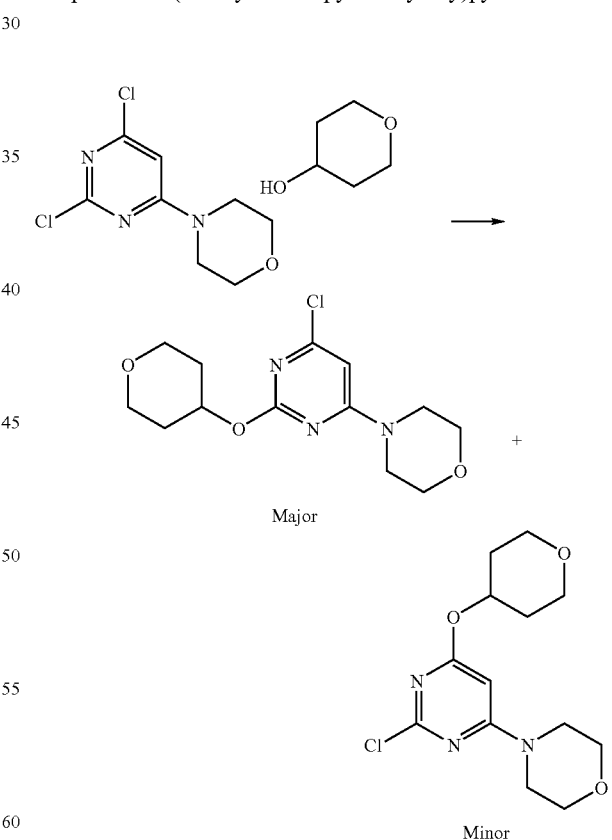

A suspension of 2,4-dichloro-6-morpholinopyrimidine (750 mg, 3.20 mmol) and sodium hydride (60%, 135 mg, 3.36 mmol) in THF (45 mL) was cooled to 0° C. under N$_2$. After stirring for 15 minutes, a solution of tetrahydro-2H-pyran-4-ol (0.320 mL, 3.36 mmol) in THF (25 mL) was added drop-wise over 45 minutes. The solution was stirred for 13 hours as the ice bath warmed to room temperature. About 65% of starting material were detected by LC, and another 1.05 equivalents of sodium hydride (135 mg, 3.36 mmol) and tetrahydro-2H-pyran-4-ol (0.320 mL, 3.36 mmol) were added. The mixture was stirred for another 14 hours. The reaction mixture was treated with EtOAc (350 mL) and NaHCO$_{3(sat.)}$ (75 mL). The organic layer was separated, washed with water (50 mL), then brine (50 mL), dried over Na$_2$SO$_4$, concentrated, and purified by silica gel chromatography (30-40% EtOAc/hexanes) to yield the two regioisomers as white solids: 4-chloro-6-morpholino-2-(tetrahydro-2H-pyran-4-yloxy)pyrimidine as the major isomer (620 mg, 65%) and 2-chloro-4-morpholino-6-tetrahydro-2H-pyran-4-yloxy)pyrimidine as the minor (95.4 mg, 10%).

4-chloro-6-morpholino-2-(tetrahydro-2H-pyran-4-yloxy) pyrimidine: LCMS (m/z): 300.0 (MH$^+$); $^1$H NMR (DMSO-d$_6$, 300 MHz): δ 6.61 (s, 1H), 5.02 (m, 1H), 3.79-3.85 (m, 2H), 3.54-3.68 (m, 8H), 3.44-3.52 (m, 2H), 1.92-2.01 (m, 2H), 1.54-1.68 (m, 2H).

2-Chloro-4-morpholino-6-(tetrahydro-2H-pyran-4-yloxy) pyrimidine: LCMS (m/z): 300.0 (MH$^+$); $^1$H NMR (DMSO-d$_6$, 300 MHz): δ 6.11 (s, 1H), 5.10 (m, 1H), 3.79-3.85 (m, 2H), 3.44-3.64 (m, 10H), 1.92-2.01 (m, 2H), 1.54-1.68 (m, 2H).

Method 3

Preparation of 2,6-dichloro-N-(6-methoxypyridin-3-yl)pyrimidin-4-amine

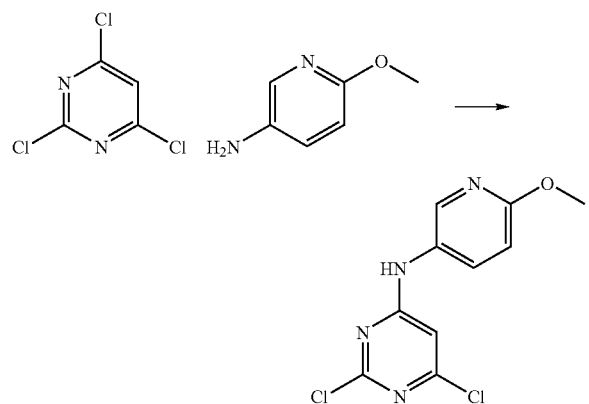

A solution of 2,4,6-trichloropyrimidine (2.0 mL, 17.4 mmol), 3-amino-6-methoxypyridine (1.5 mL, 19.1 mmol) and diisopropylethylamine (6.1 mL, 34.8 mmol) in acetonitrile (100 mL) was stirred at 55° C. under N$_2$ for 15 hours. The reaction mixture was then partitioned between EtOAc (400 mL) and NaHCO$_{3(sat.)}$ (100 mL). The organic layer was separated, washed with brine (75 mL), dried over Na$_2$SO$_4$, concentrated, and purified by silica gel chromatography (20-30% EtOAc/hexanes) to yield 2,6-dichloro-N-(6-methoxypyridin-3-yl)pyrimidin-4-amine (2.51 g, 53%) as an off-white solid. LCMS (m/z): 270.9 and 272.9 (MH$^+$); $^1$H NMR (CDCl$_3$): δ 8.13 (d, J=2.7 Hz, 1H), 8.55 (dd, J=8.5, 2.7 Hz, 1H), 6.84 (d, J=8.4 Hz, 1H), 6.84 (bs, 1H), 6.35 (s, 1H), 3.97 (s, 3H).

Method 4

Preparation of 6-chloro-N-(6-methoxypyridin-3-yl)-2-morpholinopyrimidin-4-amine and 2-chloro-N-(6-methoxypyridin-3-yl)-6-morpholinopyrimidin-4-amine

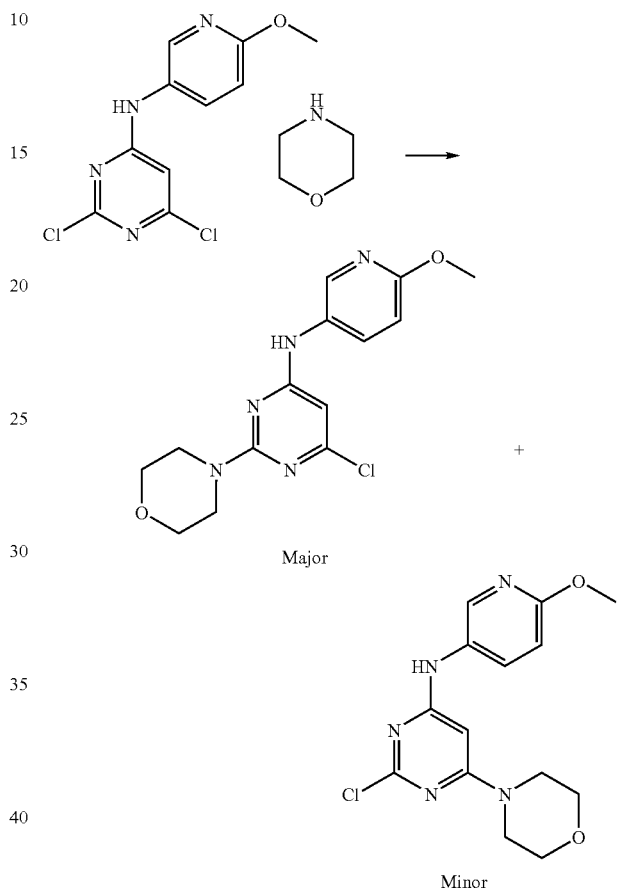

A solution of 2,6-dichloro-N-(6-methoxypyridin-3-yl)pyrimidin-4-amine (2.00 g, 7.36 mmol), morpholine (0.835 mL, 9.57 mmol), and diisopropylethylamine (1.92 mL, 11.04 mmol) in ACN (30 mL), was stirred at 45° C. under N$_2$ for 13 hours. The reaction mixture was then partitioned between EtOAc (200 mL) and NaHCO$_{3(sat.)}$ (50 mL). The organic layer was separated, washed with brine (25 mL), dried over Na$_2$SO$_4$, concentrated, and purified by silica gel chromatography (30-55% EtOAc/hexanes) to yield the two regioisomers as white solids: 6-chloro-N-(6-methoxypyridin-3-yl)-2-morpholinopyrimidin-4-amine as major (2.49 g, 84%) and 2-chloro-N-(6-methoxypyridin-3-yl)-6-morpholinopyrimidin-4-amine as minor (366 mg, 12%).

6-chloro-N-(6-methoxypyridin-3-yl)-2-morpholinopyrimidin-4-amine: LCMS (m/z): 322.0 (MH$^+$); $^1$H NMR (CDCl$_3$): δ 8.14 (d, J=3 Hz, 1H), 7.57 (dd, J=8.7, 3 Hz, 1H), 6.77 (d, J=8.7 Hz, 1H), 6.30 (bs, 1H), 5.80 (s, 1H), 3.94 (s, 3H), 3.71-3.77 (m, 8H).

2-chloro-N-(6-methoxypyridin-3-yl)-6-morpholinopyrimidin-4-amine: LCMS (m/z): 322.0 (MH$^+$); $^1$H NMR (CDCl$_3$): δ 8.11(d, J=2.7 Hz, 1H), 7.50(dd, J=8.7, 2.7 Hz, 1H), 6.80(d, J=8.6 Hz, 1H), 6.48(bs, 1H), 5.37(s, 1H), 3.95(s, 3H), 3.69-3.73(m, 4H), 3.46-3.50(m, 4H).

Method 5

Synthesis of 2,4-dichloro-6-(3-(methylsulfonyl)phenyl)pyrimidine

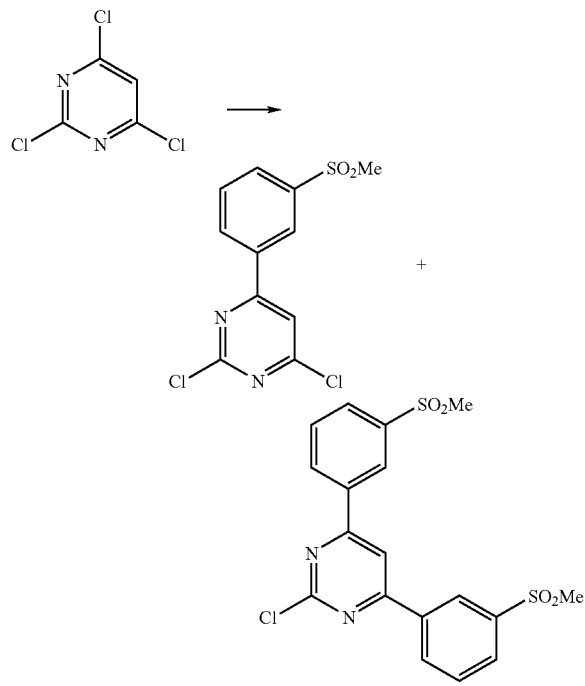

A mixture of trichloropyrimidine (1 g, 5.45 mmol), 3-(methylsulfonyl)phenylboronic acid (1.2 g, 6.00 mmol, 1.1 eq) and Pd(dppf)Cl$_2$-CH$_2$Cl$_2$ (224 mg, 0.27 mmol, 0.05 eq) in DME: 2 M Na$_2$CO$_3$ (3:1, 12 mL) was heated at 85° C. for 2 h. The reaction mixture was cooled down to room temperature and LCMS analysis revealed a mixture of 2,4-dichloro-6-(3-(methylsulfonyl)phenyl)pyrimidine and 2-chloro-4,6-bis(3-(methylsulfonyl)phenyl)pyrimidine (3:2). EtOAc (200 mL) was added, followed by water (40 mL), a solid crashed out and was filtered off. The solid was mostly 2-chloro-4,6-bis (3-(methylsulfonyl)phenyl)pyrimidine. The organic layer was separated, washed with brine (25 mL) and dried (Na$_2$SO$_4$). The solvent was concentrated under reduced pressure and the residue was purified by column chromatography on silicagel (30% EtOAc/Hexanes) to obtained the desired 2,4-dichloro-6-(3-(methylsulfonyl)phenyl)pyrimidine. LC-MS (m/z): 302.8 (MH$^+$), Rt: 1.51 min.

Method 6

Synthesis of 4-(2-chloro-6-(3-(methylsulfonyl)phenyl)pyrimidin-4-yl)morpholine

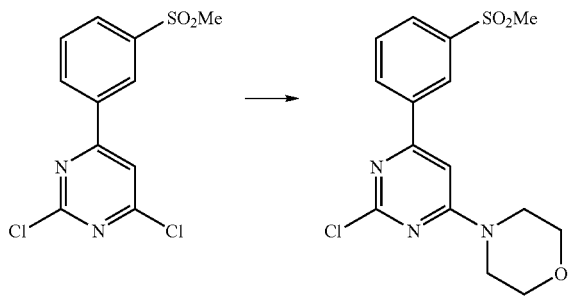

2,4-dichloro-6-(3-(methylsulfonyl)phenyl)pyrimidine (220 mg, 0.72 mmol, 1 eq) was dissolved in EtOH (5 mL) and DIEA was added (0.31 mL, 2.2 mmol, 3 eq). The reaction mixture was cooled to 0° C. and morpholine (94 mg, 1.1 μmol, 1.6 eq) was added. The reaction mixture was stirred at room temperature for 3 days. The ethanol was concentrated under reduced pressure and the residue was partitioned between EtOAc and sat. aq. NaHCO$_3$. The organic layer was separated, washed with water and dried (Na$_2$SO$_4$). The residue was purified by column chromatography on silica gel (3% EtOAc/DCM to 40% EtOAc/DCM) to obtained the desired product (150 mg, 58%). LCMS (m/z): 302.8 (MH$^+$), Rt: 1.51 min.

Method 7

Synthesis of 5-bromo-4-(trifluoromethyl)-2-pyridylamine

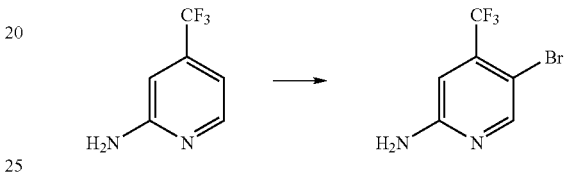

To a solution of 2-amino-4-trifluoromethylpyridine (10.0 g, 62.1 mmol) in chloroform (200 mL) was added NBS (12.0 g, 67.4 mmol). The solution was stirred in the dark for 2 hours, at which time it was added to DCM (200 mL) and 1N NaOH (200 mL). Upon mixing, the layers were separated and the organic layer was washed with NaCl$_{(sat.)}$ (100 mL), dried over Na$_2$SO$_4$, filtered and concentrated. The crude material was purified by Silica gel chromatography (0-5% EtOAc/CH$_2$Cl$_2$) yielding 12.0 g (80%) of 5-bromo-4-(trifluoromethyl)-2-pyridylamine: LCMS (m/z): 241/243 (MH$^+$); $^1$H NMR (CDCl$_3$): δ 8.28(s, 1H), 6.77(s, 1H), 4.78(bs, 2H).

Method 8

Synthesis of 5-(4,4,5,5-tetramethyl(1,3,2-dioxaborolan-2-yl))-4-(trifluoromethyl)-2-pyridylamine

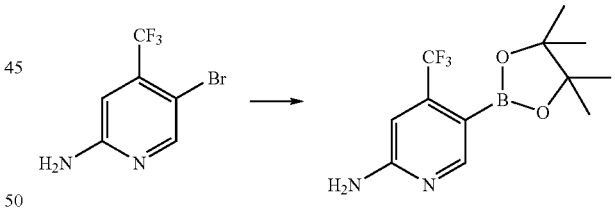

To a dry 500 mL flask was added 5-bromo-4-(trifluoromethyl)-2-pyridylamine (11.8 g, 49.0 mmol), potassium acetate (14.4 g, 146.9 mmol), 4,4,5,5-tetramethyl-2-(4,4,5,5-tetramethyl-1,3,2-dioxaborolan-2-yl)-1,3,2-dioxaborolane (13.6 g, 53.9 mmol) and dioxane (300 mL). Argon was bubbled through the solution for 15 minutes, at which time 1,1'-bis(diphenylphosphino)ferrocene palladium(II) chloride dichloromethane adduct (2.0 g, 2.45 mmol) was added. The reaction was refluxed in a 115° C. oil bath for 8 hours under argon. After cooling to room temperature, the dioxane was removed in vacuo. EtOAc (500 mL) was added, and the resulting slurry was sonicated and filtered. Additional EtOAc (500 mL) was used to wash the solid. The combined organic extracts were concentrated and the crude material was partially purified by silica gel chromatography (30-40% EtOAc/Hexanes). Upon removal of solvent, hexanes (75 mL) was added; after sonication, the resulting solid was filtered and dried on a high vacuum for 3 days yielding 2.4 g of an off-white solid. By ¹H NMR the material was a 5:1 mixture of boronate ester and 2-amino-4-trifluoromethylpyridine byproduct. The material was used as is in subsequent Suzuki reactions: LCMS (m/z): 207 (MH⁺ of boronic acid, deriving from in situ product hydrolysis on LC); ¹H NMR (CDCl₃): δ 8.50 (s, 1H), 6.72 (s, 1H), 4.80 (bs, 2H), 1.34 (s, 12H).

Method 9

Synthesis of 5-bromo-4-(trifluoromethyl)pyrimidin-2-amine

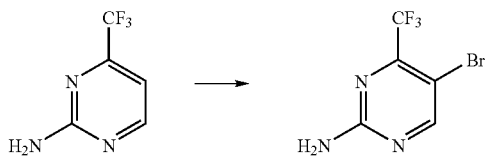

To a solution of 2-amino-4-trifluoromethylpyrimidine (8.0 g, 49.1 mmol) in chloroform (300 mL) was added N-bromosuccinimide (8.9 g, 50 mmol). The solution was stirred in the dark for 16 hours, at which time additional N-bromosuccinimide (4.0 g, 22.5 mmol) was added. After stirring for an additional 4 hours the solution was added to CH₂Cl₂ (200 mL) and 1N NaOH (200 mL). Upon mixing, the layers were separated and the organic layer was washed with NaCl$_{(sat.)}$ (100 mL), dried over Na₂SO₄, filtered and concentrated, yielding 10.9 g (82%) of 5-bromo-4-(trifluoromethyl)-2-pyrimidylamine: LCMS (m/z): 242/244 (MH⁺); ¹H NMR (CDCl₃): δ 8.52 (s, 1H), 5.38 (bs, 2H).

Method 10

Synthesis of 5-(4,4,5,5-tetramethyl(1,3,2-dioxaborolan-2-yl))-4-(trifluoromethyl)pyrimidine-2-ylamine

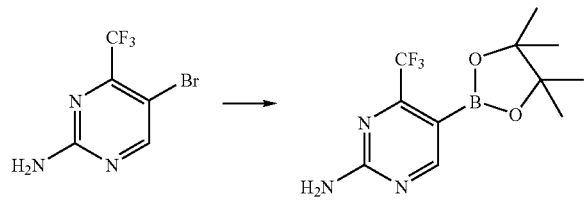

To a dry 500 mL flask was added 5-bromo-4-(trifluoromethyl)-2-pyrimidylamine (10.1 g, 41.7 mmol), potassium acetate (12.3 g, 125.2 mmol), 4,4,5,5-tetramethyl-2-(4,4,5,5-tetramethyl-1,3,2-dioxaborolan-2-yl)-1,3,2-dioxaborolane (11.6 g, 45.9 mmol) and dioxane (150 mL). Argon was bubbled through the solution for 15 minutes, at which time 1,1'-bis(diphenylphosphino)ferrocene palladium (II) chloride (1.7 g, 2.1 mmol) was added. The reaction was refluxed in a 115° C. oil bath for 6 hours under argon. After cooling to room temperature, the dioxane was removed in vacuo. EtOAc (500 mL) was added and the resulting slurry was sonicated and filtered. Additional EtOAc (500 mL) was used to wash the solid. The combined organic extracts were concentrated and the crude material was purified by silica gel chromatography (30-40% EtOAc/hexanes) yielding 4.40 g of an off white solid. By ¹H NMR the material was a 1:1 mixture of boronate ester and 2-amino-4-trifluoromethylpyrimidine byproduct. The material was used as is in subsequent Suzuki reactions.

LCMS (m/z): 208 (MH⁺ of boronic acid, deriving from in situ product hydrolysis on LC); ¹H NMR (CDCl₃): δ 8.72 (s, 1H), 5.50 (bs, 2H), 1.34 (s, 12H).

Method 11

Synthesis of 5-bromopyrimidine-2,4-diamine

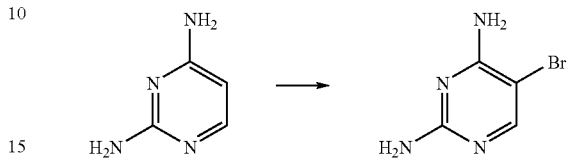

To a solution of 2,4-diaminopyrimidine (1.0 g, 9.1 mmol) in chloroform (30 mL) was added N-bromosuccinimide (1.62 g, 9.08 mmol). The solution was stirred in the dark for 12 hours, at which time it was added to CH₂Cl₂ (150 mL) and 1N NaOH (50 mL). The solid that formed was filtered, rinsed with water and concentrated in vacuo, yielding 1.4 g (74%) of 5-bromopyrimidine-2,4-diamine: LCMS (m/z): 189/191 (MH⁺); ¹H NMR (DMSO-d6): δ 7.78 (s, 1H), 6.58 (bs, 2H), 6.08 (bs, 2H).

Method 12

Synthesis of 5-(4,4,5,5-tetramethyl-1,3,2-dioxaborolan-2-yl)pyrimidine-2,4-diamine

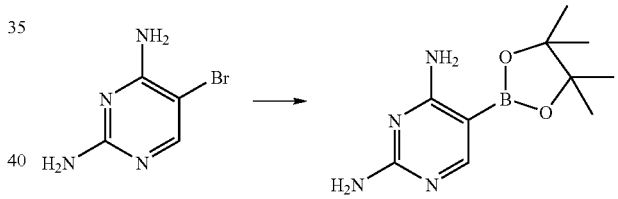

To a dry 1 L flask was added 5-bromopyrimidine-2,4-diamine (30.0 g, 158.7 mmol), potassium acetate (45.8 g, 466.7 mmol), 4,4,5,5-tetramethyl-2-(4,4,5,5-tetramethyl-1,3,2-dioxaborolan-2-yl)-1,3,2-dioxaborolane (51.16 g, 202.2 mmol) and dioxane (500 mL). Argon was bubbled through the solution for 15 minutes, at which time 1,1'-bis(diphenylphosphino)ferrocene palladium(II) chloride (2.53 g, 3.11 mmol) was added. The reaction was refluxed in a 115° C. oil bath for 16 hours under argon. After cooling to room temperature, the solid inorganic material was filtered, rinsed with EtOAc (1 L). The organic filtrate was concentrated in vacuo and to the resulting solid was added dichloromethane (1 L). After sonication the solid was filtered. The solid was the debrominated 2,4-diaminopyrimidine. The filtrate containing desired boronate ester was concentrated in vacuo. To this residue was added diethyl ether (100 mL). After sonication, the solution was filtered, rinsed with additional diethyl ether (50 mL) and the solid obtained was dried under high vacuum to yield the desired 2,4-diaminopyrimidyl-5-boronate ester (10.13 g, 27%). By ¹H NMR the material was a 4:1 mixture of 2,4-diaminopyrimidyl-5-boronate ester and 2,4-diaminopyrimidine byproduct. The material was used as is in subsequent Suzuki reactions LCMS (m/z): 155 (MH⁺ of boronic acid, deriving from in situ product hydrolysis on LC); $^1$H NMR (CDCl$_3$+CD$_3$OD): δ 8.16 (s, 1H), 1.34 (s, 12H).

Method 13

Synthesis of 4-methoxypyrimidine-2-ylamine

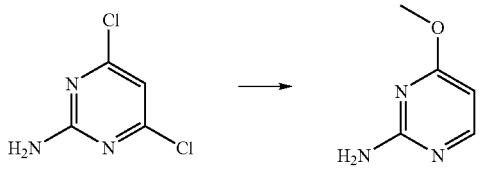

To a solution of 4,6-dichloro-2-amino pyrimidine (5.0 g, 30.5 mmol) in MeOH (100 mL) was added 25% sodium methoxide (6.59 g, 30.5 mmol). The solution was refluxed for 20 hours, at which time the methanol was removed in vacuo. The residue was dissolved in EtOAc (350 mL), washed with H$_2$O (100 mL) and with NaCl$_{(sat.)}$ (100 mL), dried over Na$_2$SO$_4$, filtered and concentrated yielding 4.4 g (90%) of 4-chloro-6-methoxypyrimidine-2-ylamine.

To a solution of 4-chloro-6-methoxypyrimidine-2-ylamine (4.4 g, 27.7 mmol) in EtOAc (200 mL) and ethanol (150 mL), was added diisopropylethylamine (9.6 mL, 55.3 mmol) and 10% palladium on carbon (2.9 g, 2.77 mmol). The heterogeneous solution was stirred under a balloon atmosphere of H$_2$ for 14 hours, at which time the solution was filtered through a Celite pad and the volatiles were removed in vacuo. The residue was dissolved in EtOAc (200 mL), washed with Na$_2$CO$_{3(sat)}$ (100 mL) and with NaCl$_{(sat.)}$ (100 mL), dried over Na$_2$SO$_4$, filtered and concentrated yielding 3.1 g (90%) of 4-methoxypyrimidine-2-ylamine. LCMS (m/z): 126 (MH$^+$). $^1$H NMR (CDCl$_3$): δ 8.00 (d, J=5.7 Hz, 1H), 6.08 (d, J=5.7 Hz, 1H), 4.98 (bs, 2H), 3.84 (s, 3H).

Method 14

Synthesis of 5-bromo-4-methoxypyrimidine-2-ylamine

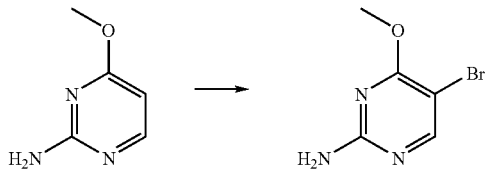

To a solution of 4-methoxypyrimidine-2-ylamine (1.84 g, 14.7 mmol) in chloroform (600 mL) was added N-bromosuccinimide (2.62 g, 14.7 mmol). After stirring in the dark for 5 hours, the solution was added to CH$_2$Cl$_2$ (200 mL) and 1N NaOH (100 mL). Upon mixing, the layers were separated and the organic layer was washed with NaCl$_{(sat.)}$ (100 mL), dried over Na$_2$SO$_4$, filtered and concentrated yielding 2.88 g (96%) of 5-bromo-4-methoxypyrimidine-2-ylamine. LCMS (m/z): 204/206 (MH$^+$). $^1$H NMR (CDCl$_3$): δ 8.10 (s, 1H), 4.93 (bs, 2H), 3.96 (s, 3H).

Method 15

Synthesis of 4-methoxy-5-(4,4,5,5-tetramethyl-(1,3,2-dioxaborolan-2-yl))pyrimidine-2-ylamine

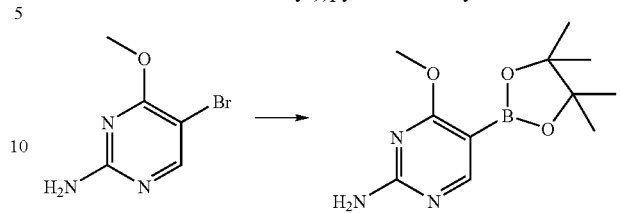

To a dry 200-mL flask was added 5-bromo-4-methoxypyrimidine-2-ylamine (2.88 g, 14.1 mmol), potassium acetate (4.16 g, 42.4 mmol), 4,4,5,5-tetramethyl-2-(4,4,5,5-tetramethyl-1,3,2-dioxaborolan-2-yl)-1,3,2-dioxaborolane (3.76 g, 14.8 mmol) and dioxane (75 mL). Argon was bubbled through the solution for 15 minutes, at which time 1,1'-bis(diphenylphosphino)ferrocene palladium(II) chloride dichloromethane adduct (0.58 g, 0.71 mmol). The reaction was refluxed in a 115° C. oil bath for 21 hours under argon. After cooling to room temperature, the dioxane was removed in vacuo. EtOAc (500 mL) was added and the resulting slurry was sonicated and filtered. Additional EtOAc (500 mL) was used to wash the solid. The combined organics were concentrated and the crude material was purified by silica gel chromatography (EtOAc as eluent) yielding 2.4 g of an off white solid. By $^1$H NMR the material was a 1:1 mixture of boronate ester and 4-methoxypyrimidine-2-ylamine. The material was used as is in subsequent Suzuki reactions. LCMS (m/z): 170 (MH$^+$ of boronic acid, deriving from in situ product hydrolysis on LC); $^1$H NMR (CDCl$_3$): δ 8.42 (s, 1H), 5.22 (bs, 2H), 3.90 (s, 3H), 1.34 (s, 12H).

Method 16

Synthesis of N-(5-carbamimidoylpyridin-2-yl)pivalamide

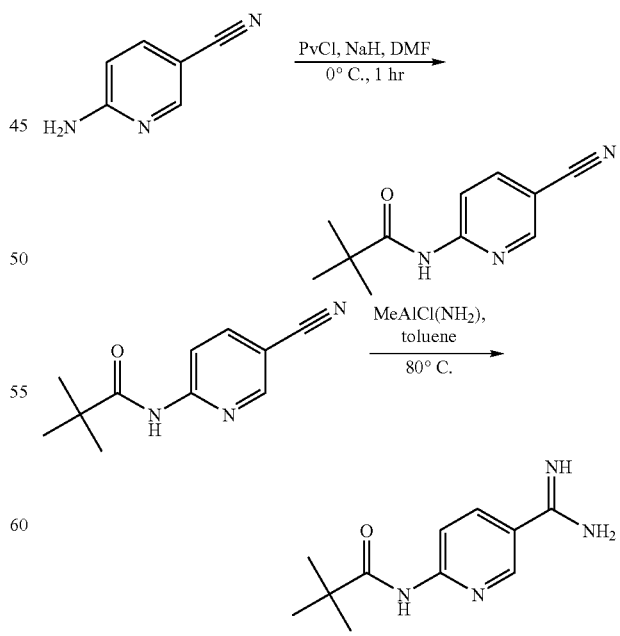

A suspension of commercially available 2-amino-5-cyanopyridine (750 mg, 6.3 mmol) and sodium hydride 60% (264 mg, 6.61 mmol) in 45 mL of DMF, is cooled to 0° C. under N$_2$.

After stirring for 15 minutes, a solution of trimethylacetyl chloride (0.814 mL, 6.61 mmol) in 25 mL DMF is added drop-wise over 15 minutes. The solution is stirred for 13 hours as the ice bath warms to room temperature. At this time the reaction mixture is partitioned between EtOAc (350 mL) and NaHCO$_{3(sat.)}$ (75 mL). The organic layer is separated, washed with water (50 mL), then brine (50 mL), dried over Na$_2$SO$_4$, filtered, concentrated. The crude product thus obtained is dried under high-vacuum and used as is in the next step.

A mixture of N-(5-cyanopyridin-2-yl)pivalamide (1.22 g, 6.00 mmol) and MeAl(Cl)NH$_2$ (18 mL, 0.67M solution in toluene, 12.00 mmol) in 25 mL toluene is heated at 80° C. for 15 hours. The resulting N-(5-carbamimidoylpyridin-2-yl)pivalamide is used without further purification.

Method 17

Synthesis of N-(5-(4-hydroxy-6-oxo-1,6-dihydropyrimidin-2-yl)pyridin-2-yl)pivalamide

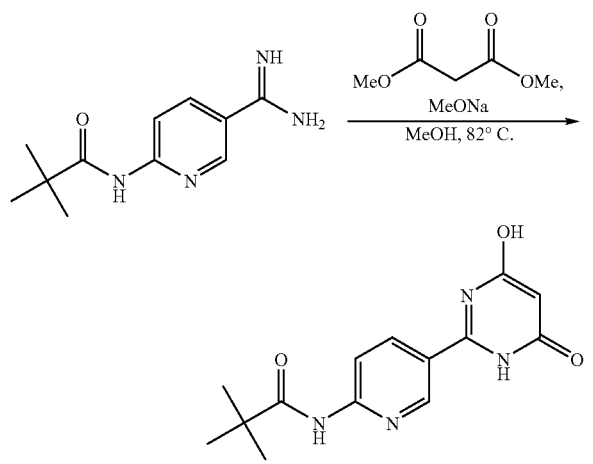

A suspension of sodium methoxide (432 mg, 8.0 mmol), N-(5-carbamimidoylpyridin-2-yl)pivalamide (880 mg, 4.0 mmol) and dimethylmalonate (457 µL, 4.0 mmol) in 15 mL methanol is refluxed at 82° C. for 14 hours. The resulting suspension is dissolved in 15 mL water and acidified using 6M HCl. The precipitate is filtered, rinsed with water, air/vacuum dried and used in the next step without further purification.

Method 18

Synthesis of N-(5-(4-chloro-6-morpholinopyrimidin-2-yl)pyridin-2-yl)pivalamide

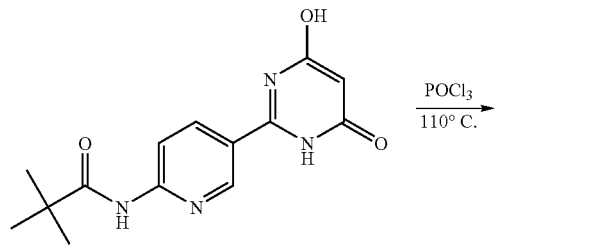

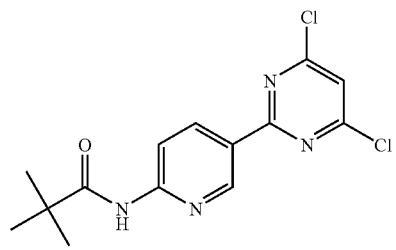

N-(5-(4-hydroxy-6-oxo-1,6-dihydropyrimidin-2-yl)pyridine-2-yl)pivalamide (907 mg, 3.14 mmol) is refluxed in phosphoryl trichloride (10 mL) for 13 hours, concentrated and purified by SiO$_2$ chromatography.

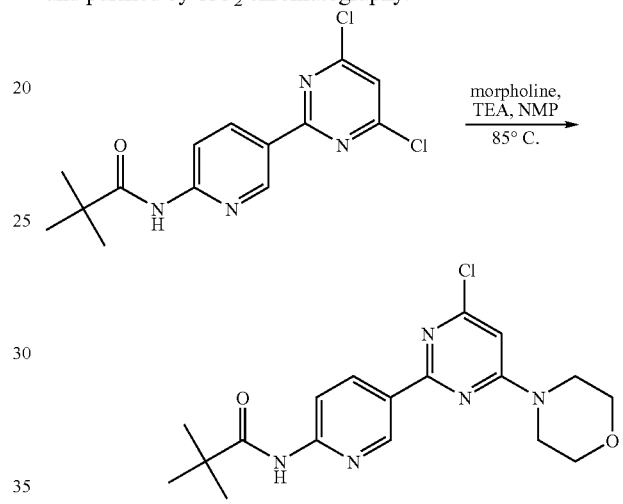

N-(5-(4,6-dichloropyrimidin-2-yl)pyridine-2-yl)pivalamide (975 mg, 3.0 mmol), morpholine (0.262 mL, 3.0 mmol) and triethylamine (502 mL, 3.6 mmol) are stirred in NMP (10 mL) for 2 hours at 85° C. At this time the reaction mixture is partitioned between EtOAc (200 mL) and NaHCO$_{3(sat.)}$ (50 mL). The organic layer is separated, washed with water (30 mL), then brine (30 mL), dried over Na$_2$SO$_4$, filtered, concentrated, obtaining the desired product.

Methods 19-21

Preparation of N-(4-chloro-6-morpholino-4'-(trifluoromethyl)-2,5'-bipyrimidin-2'-yl)pivalamide; N,N'-(4-chloro-6-morpholino-2,5'-bipyrimidine-2',4'-diyl)bis(2,2-dimethylpropanamide); and N-(4-chloro-6-morpholino-2,5'-bipyrimidin-2'-yl)pivalamide

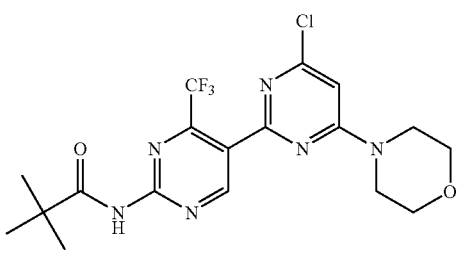

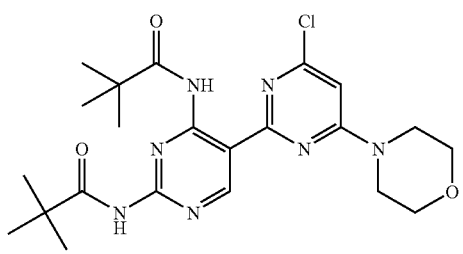

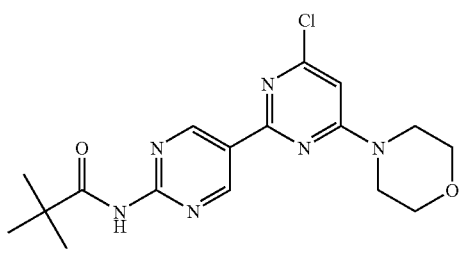

N-(4-chloro-6-morpholino-4'-(trifluoromethyl)-2,5'-bipyrimidin-2'-yl)-pivalamide, N,N'-(4-chloro-6-morpholino-2,5'-bipyrimidine-2',4'-diyl)bis(2,2-dimethyl-propanamide), and N-(4-chloro-6-morpholino-2,5'-bipyrimidin-2'-yl)pivalamide are prepared according to Methods 16-18.

Method 22

Synthesis of 2,6-dichloro-4,5'-bipyrimidin-2'-amine

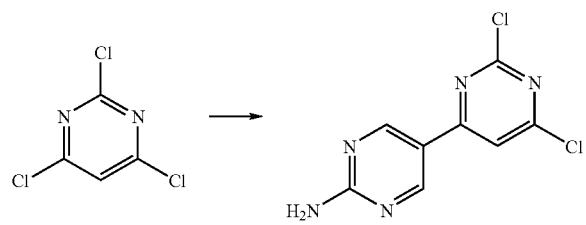

According to Method 5, the reaction of 2,4,6-trichloropyrimidine with 5-(4,4,5,5-tetramethyl-1,3,2-dioxaborolan-2-yl)pyrimidin-2-amine in the presence of Pd(dppf)Cl$_2$-CH$_2$Cl$_2$ in DME and 2 M Na$_2$CO$_3$ (3:1) gave 2,6-dichloro-4,5'-bipyrimidin-2'-amine in 48% yield. LCMS (m/z): 241.1 (MH$^+$), Rt 2.05 min.

Method 23

Synthesis of 2-chloro-6-morpholino-4,5'-bipyrimidin-2'-amine

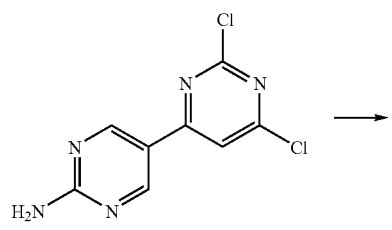

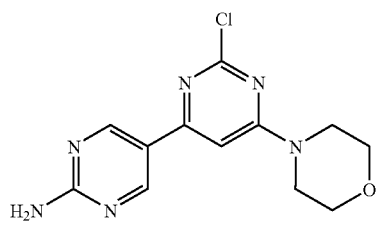

According to Method 6, the reaction of 2,6-dichloro-4,5'-bipyrimidin-2'-amine with morpholine in acetonitrile gave 2-chloro-6-morpholino-4,5'-bipyrimidin-2'-amine. LCMS (m/z): 293.0 (MH$^+$); Rt 1.92 min.

Method 24

Synthesis of 2,6-dichloro-N-methyl-4,5'-bipyrimidin-2'-amine

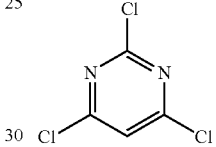 

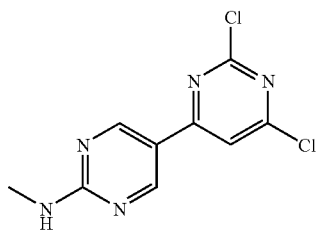

According to Method 5, the reaction of 2,4,6-trichloropyrimidine with 5-(4,4,5,5-tetramethyl-1,3,2-dioxaborolan-2-yl)pyrimidin-2-amine in the presence of Pd(dppf)Cl$_2$-CH$_2$Cl$_2$ in DME and 2 M Na$_2$CO$_3$ (3:1) gave 2,6-dichloro-N-methyl-4,5'-bipyrimidin-2'-amine.

Method 25

Synthesis of 2-chloro-N-methyl-6-morpholino-4,5'-bipyrimidin-2'-amine

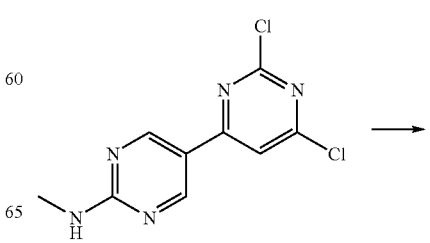

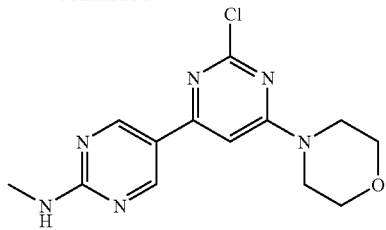

According to Method 6, the reaction of 2,6-dichloro-N-methyl-4,5'-bipyrimidin-2'-amine with morpholine in acetonitrile gave 2-chloro-N-methyl-6-morpholino-4,5'-bipyrimidin-2'-amine.

Method 26

Synthesis of 4,6-dichloro-2-(tetrahydro-2H-pyran-4-yl)pyrimidine

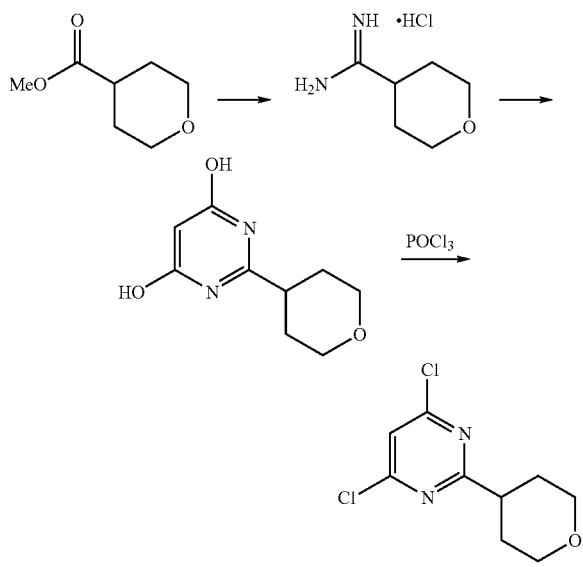

To a suspension of ammonium chloride (8.02 g, 150 mmol) in toluene at 0° C. was added trimethylaluminum in hexane (2 M, 75 mL, 150 mmol) over 20 min. After being stirred at rt for 25 min, methyl tetrahydro-2H-pyran-4-carboxylate (4.32 g, 30 mmol) was added. The reaction mixture was heated for 18 h at 80° C. The reaction mixture was cooled down to 0° C., dry methanol was added carefully. After stirring for 20 min at 0° C., the white precipitate was filtered off, washed with methanol. The filtrate was concentrated, treated again with methanol, and then 1:1 methanol/DCM. The final filtrate was concentrated and dried to give tetrahydro-2H-pyran-4-carboximidamide as its HCl salt (4.68 g).

To a suspension of sodium hydride (3.0 g, 60% in oil, 75 mmol) in hexane (4 mL) was added ethanol (60 mL) slowly at rt. After 30 min at rt, diethyl malonate (4 g, 25 mmol) were added, followed by tetrahydro-2H-pyran-4-carboximidamide-HCl (4.12 g, 25 mmol). The mixture was heated at 90° C. overnight. Dry molecular sieves (2.5 g) were added, and additional ethanol was added to help stirring. The reaction was heated at 90° C. for 4 days. The reaction mixture was cooled to room temperature and filtered through Celite. The filtrate was removed in vacuo to give 2-(tetrahydro-2H-pyran-4-yl)pyrimidine-4,6-diol as a solid, which was used for next step without further purification.

A mixture of 2-tetrahydro-2H-pyran-4-yl)pyrimidine-4,6-diol (1 equiv), POCl₃ (40 equiv) and a few drops of DMF was heated at 115° C. for 4 h, then cooled to RT. Excess POCl₃ was removed to give a semi-solid. The solid was cooled, and treated with (1:1) ethyl acetate/hexane and aq. sodium bicarbonate was added carefully until basic. The aqueous layer was extracted with (1:1) ethyl acetate/hexane. The combined organic layers were washed with water and brine, dried over sodium sulfate, and concentrated to give 4,6-dichloro-2-(tetrahydro-2H-pyran-4-yl)pyrimidine (2.49 g, 43%).

Method 27

Synthesis of 6-chloro-2-(tetrahydro-2H-pyran-4-yl)-4,5'-bipyrimidin-2'-amine

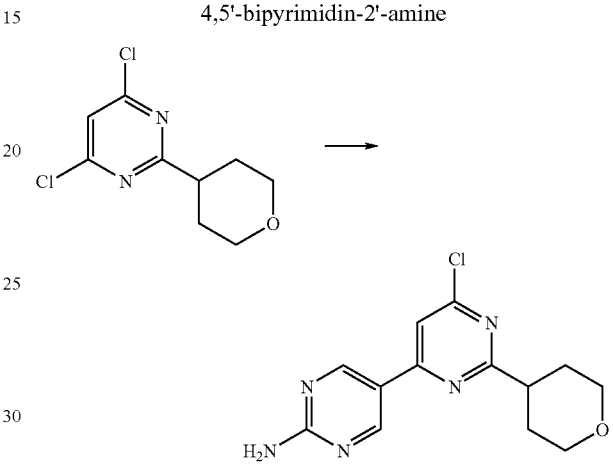

A mixture of 4,6-dichloro-2-(tetrahydro-2H-pyran-4-yl)pyrimidine (300 mg, 1.29 mmol), 5-(4,4,5,5-tetramethyl-1,3,2-dioxaborolan-2-yl)pyrimidin-2-amine (300 mg, 1.35 mmol) in THF (12 mL) and 2M sodium carbonate (4 mL) was flushed with argon. To the mixture was added Pd(dppf)Cl₂-DCM (124 mg, 0.154 mmol). The mixture was heated at 70° C. for 2 h. The solvent was removed. To the residue was dissolved in ethyl acetate and methanol (50 mL each). The mixture was filtered to remove the solid. The filtrate was concentrated and purified on HPLC to give 6-chloro-2-(tetrahydro-2H-pyran-4-yl)-4,5'-bipyrimidin-2'-amine as its TFA salt (114 mg, 22%). LCMS (m/z): 292.0 (MH⁺). Rt: 2.04 min.

Example 1

Preparation of 5-(4-morpholino-6-(tetrahydro-2H-pyran-4-yloxy)pyrimidin-2-yl)-4-(trifluoromethyl)pyridin-2-amine

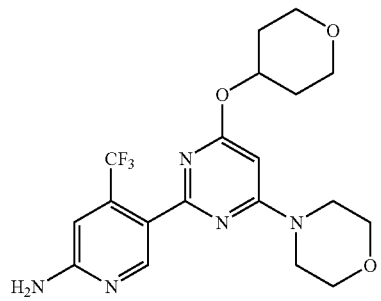

A mixture of 2-chloro-4-morpholino-6-(tetrahydro-2H-pyran-4-yloxy)pyrimidine (prepared as in Method 2, 15 mg, 0.05 mmol), 5-(4,4,5,5-tetramethyl(1,3,2-dioxaborolan-2-yl))-4-(trifluoromethyl)-2-pyridylamine (prepared as in Methods 7 and 8, 43 mg, 0.15 mmol) and Pd(dppf)Cl₂-CH₂Cl₂ (4.1 mg, 0.005 mmol) in DME: 2 M Na₂CO₃ (3:1, 1 mL) was heated under microwave irradiation for 15 minutes at 120° C. (normal absorption, fixed hold time). The reaction mixture was partitioned between EtOAc (50 mL) and H₂O (10 mL); the organic layer separated, washed with brine (7 mL), dried over Na₂SO₄, filtered, concentrated and purified directly by reverse-phase HPLC. Upon lyophilization, the TFA salt of 5-(4-morpholino-6-(tetrahydro-2H-pyran-4-yloxy)pyrimidin-2-yl)-4-(trifluoromethyl)pyridin-2-amine was obtained as a white solid (9.4 mg, 44%). LC-MS (m/z): 426.1 (MH⁺). Rt: 2.55 min.

Example 2

Preparation of 4-morpholino-6-(tetrahydro-2H-pyran-4-yloxy)-4'-(trifluoromethyl)-2,5'-bipyrimidin-2'-amine

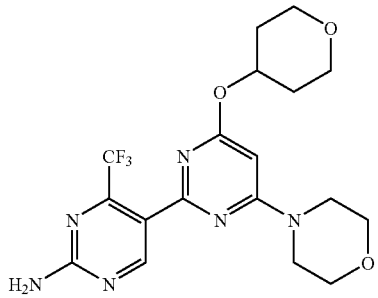

According to Example 1, the coupling reaction of 2-chloro-4-morpholino-6-(tetrahydro-2H-pyran-4-yloxy)pyrimidine with 5-(4,4,5,5-tetramethyl-(1,3,2-dioxaborolan-2-yl))-4-(trifluoromethyl)pyrimidine-2-ylamine yielded, upon purification by reverse-phase HPLC, the TFA salt of 4-morpholino-6-(tetrahydro-2H-pyran-4-yloxy)-4'-(trifluoromethyl)-2,5'-bipyrimidin-2'-amine as a white solid (23.0 mg, 99%): LCMS (m/z): 427.1 (MH⁺). Rt: 3.24 min.

Example 3

Preparation of 4-morpholino-6-(tetrahydro-2H-pyran-4-yloxy)-2,5'-bipyrimidine-2',4'-diamine

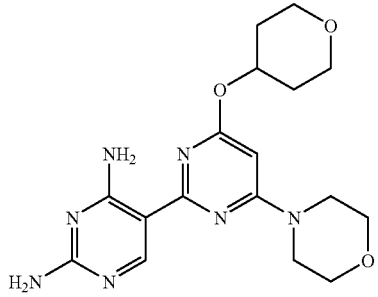

According to Example 1, the coupling reaction of 2-chloro-4-morpholino-6-(tetrahydro-2H-pyran-4-yloxy)pyrimidine with 5-(4,4,5,5-tetramethyl-1,3,2-dioxaborolan-2-yl)pyrimidine-2,4-diamine yielded upon purification by reverse-phase HPLC and lyophilization, the TFA salt of 4-morpholino-6-(tetrahydro-2H-pyran-4-yloxy)-2,5'-bipyrimidine-2',4'-diamine as a white solid (18.7 mg, 100%). LCMS (m/z): 374.1 (MH⁺). Rt: 2.16 min.

Example 4

Preparation of 2-amino-5-(4-morpholino-6-(tetrahydro-2H-pyran-4-yloxy)pyrimidin-2-yl)pyrimidin-4(3H)-one

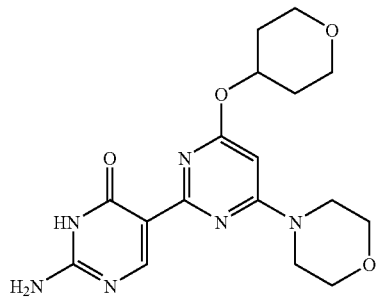

According to Example 1 the reaction of 2-chloro-4-morpholino-6-(tetrahydro-2H-pyran-4-yloxy)pyrimidine (20 mg, 0.067 mmol) with 4-methoxy-5-(4,4,5,5-tetramethyl(1,3,2-dioxaborolan-2-yl))pyrimidine-2-ylamine (50 mg, 0.200 mmol) afforded 4'-methoxy-4-morpholino-6-(tetrahydro-2H-pyran-4-yloxy)-2,5'-bipyrimidin-2'-amine. The crude product was treated with morpholine (0.058 mL, 0.667 mmol) in NMP (2 mL) and heated under microwave irradiation (high absorption, fixed hold time) for 60 minutes at 200° C. Additional morpholine (0.058 mL, 0.667 mmol) was added and the solution heated at 200° C. under microwave irradiation for another 30 minutes, then another 60 minutes at 210° C. Upon cooling the material was directly purified by reverse-phase HPLC. After lyophilization, the TFA salt of 2-amino-5-(4-morpholino-6-(tetrahydro-2H-pyran-4-yloxy)pyrimidin-2-yl)pyrimidin-4(3H)-one was isolated as an off white solid (17.1 mg, 68%), LCMS (m/z): 375.1 (MH⁺). Rt: 1.74 min.

Example 5

Preparation of 2-(6-amino-4-(trifluoromethyl)pyridin-3-yl)-N-(6-methoxypyridin-3-yl)-6-morpholinopyrimidin-4-amine

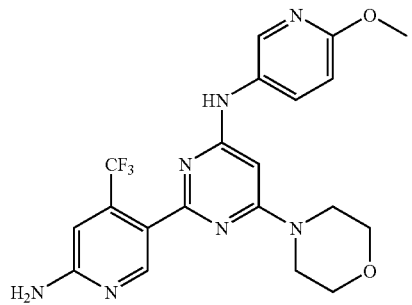

According to Example 1 the Suzuki reaction of 2-chloro-N-(6-methoxypyridin-3-yl)-6-morpholinopyrimidin-4-amine and 5-(4,4,5,5-tetramethyl(1,3,2-dioxaborolan-2-yl))-4-(trifluoromethyl)-2-pyridylamine yielded, upon purification by reverse-phase HPLC and lyophilization, the bis TFA salt of 2-(6-amino-4-(trifluoromethyl)pyridin-3-yl)-

N-(6-methoxypyridin-3-yl)-6-morpholinopyrimidin-4-amine as a white solid (13.1 mg, 47%); LCMS (m/z): 448.1 (MH+). Rt: 2.30 min.

Example 6

Preparation of N4-(6-methoxypyridin-3-yl)-6-morpholino-4'-(trifluoromethyl)-2,5'-bipyrimidine-2',4-diamine

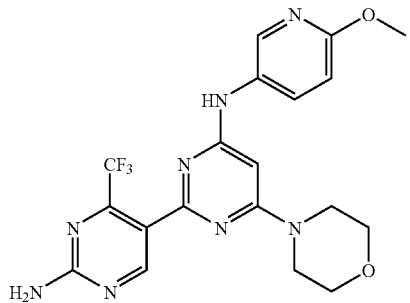

According to Example 1, the reaction of 2-chloro-N-(6-methoxypyridin-3-yl)-6-morpholinopyrimidin-4-amine with 5-(4,4,5,5-tetramethyl(1,3,2-dioxaborolan-2-yl))-4-(trifluoromethyl)pyrimidine-2-ylamine, upon purification by reverse-phase HPLC and lyophilization, gave bis-TFA salt of N-(6-methoxypyridin-3-yl)-6-morpholino-4'-(trifluoromethyl)-2,5'-bipyrimidine-2',4-diamine as a white solid (15.1 mg, 54%), LCMS (m/z): 449.1 (MH+). Rt: 2.52 min.

Example 7

Preparation of N4-(6-methoxypyridin-3-yl)-6-morpholino-2,5'-bipyrimidine-2',4,4'-triamine

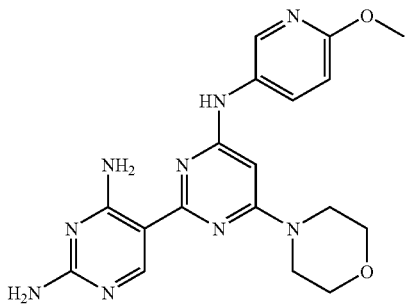

According to Example 1, the reaction of 2-chloro-N-(6-methoxypyridin-3-yl)-6-morpholinopyrimidin-4-amine with 5-(4,4,5,5-tetramethyl-1,3,2-dioxaborolan-2-yl)pyrimidine-2,4-diamine, upon purification by reverse-phase HPLC and lyophilization, gave the bis-TFA salt of N$^4$-(6-methoxypyridin-3-yl)-6-morpholino-2,5'-bipyrimidine-2',4,4'-triamine as a white solid (24.2 mg, 98%), LCMS (m/z): 396.1 (MH+). Rt: 2.14 min.

Example 8

Preparation of 2-amino-5-(4-(6-methoxypyridin-3-ylamino)-6-morpholinopyrimidin-2-yl)pyrimidin-4(3H)-one

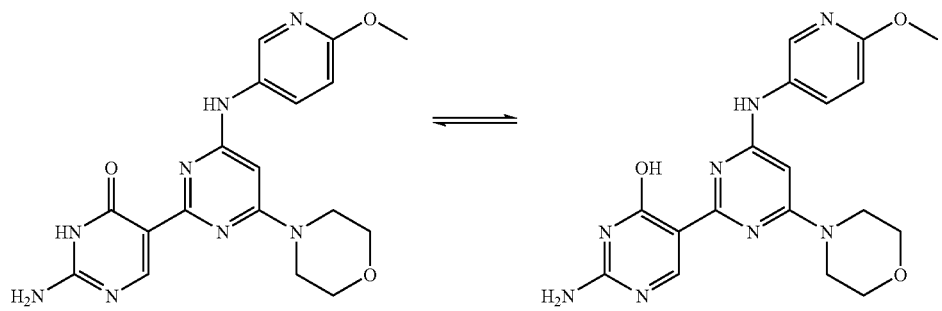

According to Example 1, the reaction of 2-chloro-N-(6-methoxypyridin-3-yl)-6-morpholinopyrimidin-4-amine (40 mg, 0.124 mmol) with 4-methoxy-5-(4,4,5,5-tetramethyl(1,3,2-dioxaborolan-2-yl))pyrimidine-2-ylamine (94 mg, 0.372 mmol) gave 4'-methoxy-N$^4$-(6-methoxypyridin-3-yl)-6-morpholino-2,5'-bipyrimidine-2',4-diamine. A mixture of crude 4'-methoxy-N$^4$-(6-methoxypyridin-3-yl)-6-morpholino-2,5'-bipyrimidine-2',4-diamine and morpholine (0.108 mL, 1.24 mmol) in N-methylpyrrolidinone (2 mL) was heated under microwave irradiation (high absorption, fixed hold time) for 20 minutes at 200° C. Additional morpholine (0.108 mL, 1.24 mmol) was added and the solution heated at 200° C. under microwave irradiation for another 50 minutes. Another portion of morpholine (0.108 mL, 1.24 mmol) was added and the mixture heated at 200° C. under microwave irradiation for 90 minutes. Upon cooling the material was directly purified by reverse-phase HPLC. After lyophilization, the bis-TFA salt of 2-amino-5-(4-(6-methoxypyridin-3-ylamino)-6-morpholinopyrimidin-2-yl)pyrimidin-4(3H)-one was isolated as an off white solid (24.6 mg, 50%): LCMS (m/z): 397.1 (MH+). Rt: 1.92 min.

Example 10

Preparation of 5-(4,6-dimorpholinopyrimidin-2-yl)-4-(trifluoromethyl)pyridin-2-amine

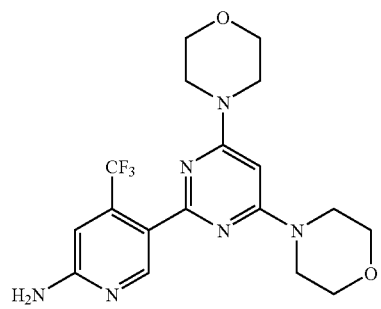

According to Example 1, the reaction of 4,6-dimorpholino-2-chloropyrimidine with 5-(4,4,5,5-tetramethyl(1,3,2-dioxaborolan-2-yl))-4-(trifluoro-methyl)-2-pyridylamine and the bis-TFA salt of 5-(4,6-dimorpholinopyrimidin-2-yl)-4-(trifluoromethyl)pyridin-2-amine as a white solid (68%): LCMS (m/z): 411.0 (MH$^+$). Rt: 2.10 min.

Example 11

Preparation of 4,6-dimorpholino-4'-(trifluoromethyl)-2,5'-bipyrimidin-2'-amine

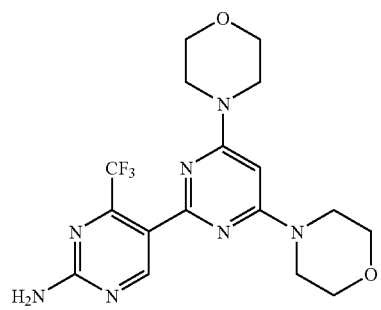

According to Example 1, the reaction of 4,6-dimorpholino-2-chloropyrimidine and 5-(4,4,5,5-tetramethyl(1,3,2-dioxaborolan-2-yl))-4-(trifluoro-methyl)pyrimidine-2-ylamine yielded the bis-TFA salt of 4,6-dimorpholino-4'-(trifluoromethyl)-2,5'-bipyrimidin-2'-amine as a white solid (40%): LCMS (m/z): 412.0 (MH$^+$). Rt: 2.28 min.

Example 12

Preparation of 4,6-dimorpholino-2,5'-bipyrimidine-2',4'-diamine

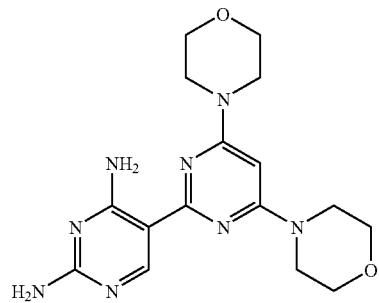

According to Example 1, the reaction of 4,6-dimorpholino-2-chloropyrimidine and 5-(4,4,5,5-tetramethyl-1,3,2-dioxaborolan-2-yl)pyrimidine-2,4-diamine gave the bis-TFA salt of 4,6-dimorpholino-2,5'-bipyrimidine-2',4'-diamine as a white solid (43%): LCMS (m/z): 359.0 (MH$^+$). Rt: 1.96 min.

Example 13

Preparation of 5-(4-(3-(methylsulfonyl)phenyl)-6-morpholino pyrimidin-2-yl)-4-(trifluoromethyl)pyridin-2-amine

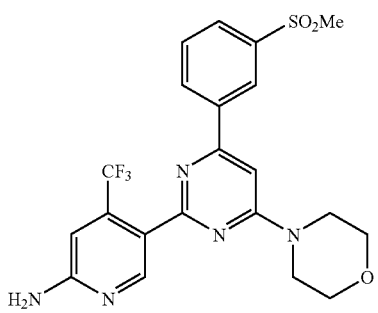

According to Example 1, the coupling reaction of 4-(2-Chloro-6-(3-(methylsulfonyl)phenyl)pyrimidin-4-yl)morpholine with 5-(4,4,5,5-tetramethyl(1,3,2-dioxaborolan-2-yl))-4-(trifluoromethyl)-2-pyridylamine (microwave irradiation at 120° C. for 15 minutes twice) and purification by reverse phase preparative HPLC, yielded the TFA salt of 5-(4-(3-(methylsulfonyl)phenyl)-6-morpholinopyrimidin-2-yl)-4-(trifluoro-methyl)pyridin-2-amine (20%). LCMS (m/z): 479.9 (M$^+$). Rt=2.50 min.

Example 14

Preparation of 4-(3-(methylsulfonyl)phenyl)-6-morpholino-4'-(trifluoromethyl)-2,5'-bipyrimidin-2'-amine

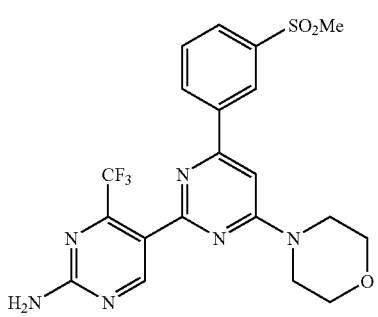

According to Example 1, the coupling reaction of 4-(2-Chloro-6-(3-(methylsulfonyl)phenyl)pyrimidin-4-yl)morpholine with 5-(4,4,5,5-tetramethyl(1,3,2-dioxaborolan-2-yl))-4-(trifluoromethyl)pyrimidine-2-ylamine (microwave irradiation at 120° C. for 15 minutes) and purification by reverse phase preparative HPLC, yielded the TFA salt of 4-(3-(methylsulfonyl)phenyl)-6-morpholino-4'-(trifluoromethyl)-2,5'-bipyrimidin-2'-amine (10%). LCMS (m/z): 480.9 (M$^+$). Rt=3.29 min.

Example 15

Preparation of N-(5-(4-(5-methoxypyridin-3-yl)-6-morpholinopyrimidin-2-yl)pyridin-2-yl)pivalamide

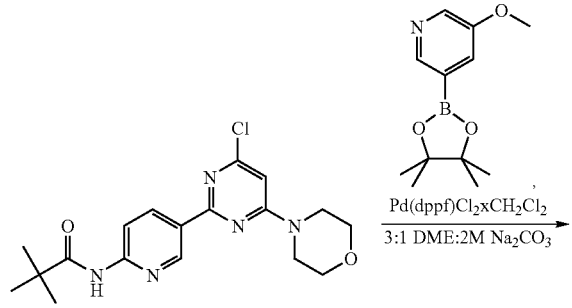

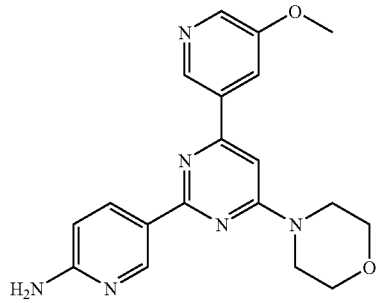

A mixture of N-(5-(4-chloro-6-morpholinopyrimidin-2-yl)pyridine-2-yl)pivalamide (50 mg, 0.133 mmol), 3-methoxy-5-(4,4,5,5-tetramethyl-1,3,2-dioxaborolan-2-yl)pyridine (94 mg, 0.399 mmol) and Pd(dppf)Cl$_2$-CH$_2$Cl$_2$ (16 mg, 0.020 mmol) in 2 mL of dimethoxyethane:2 M Na$_2$CO$_3$ (3:1) is heated under microwave irradiation for 15 minutes at 130° C. (normal absorption, fixed hold time). The reaction mixture is partitioned between EtOAc (50 mL) and H$_2$O (10 mL); the organic layer is separated, washed with brine (7 mL), dried over Na$_2$SO$_4$, filtered and concentrated. The residue thus obtained is used in the next step without further purification.

Example 16

Preparation of 5-(4-(5-methoxypyridin-3-yl)-6-morpholinopyrimidin-2-yl)pyridin-2-amine

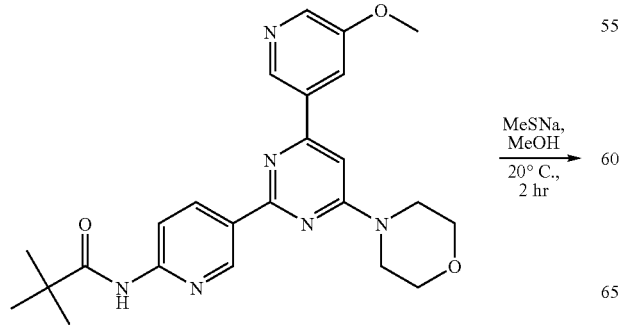

The pyvaloyl protecting group is cleaved using sodium methanethiolate in methanol. The resulting product is purified by reverse-phase HPLC and lyophilized to give 5-(4-(5-methoxypyridin-3-yl)-6-morpholinopyrimidin-2-yl)pyridin-2-amine.

The following compounds can be synthesized from the intermediates described in Methods 19-21 and commercially available 3-methoxy-5-(4,4,5,5-tetramethyl-1,3,2-dioxaborolan-2-yl)puridine via Suzuki coupling-reaction based on the above procedure: 4-(5-methoxypyridin-3-yl)-6-morpholino-4'-(trifluoromethyl)-2,5'-bipyrimidin-2'-amine, 4-(5-methoxypyridin-3-yl)-6-morpholino-2,5'-bipyrimidine-2',4'-diamine, 4-(5-methoxypyridin-3-yl)-6-morpholino-2,5'-bipyrimidin-2'-amine

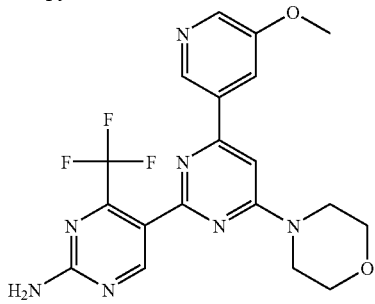

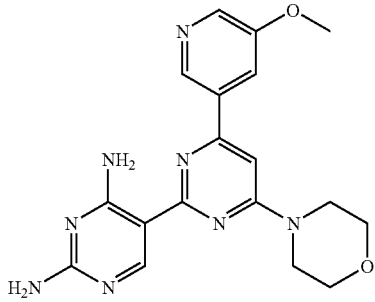

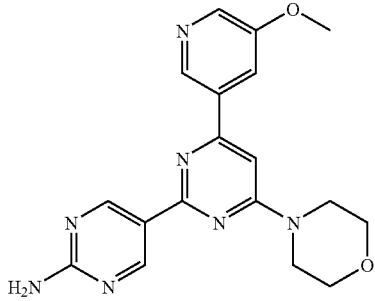

Example 17

Preparation of 6-morpholino-N²-(quinolin-3-yl)-4,5'-bipyrimidine-2,2'-diamine

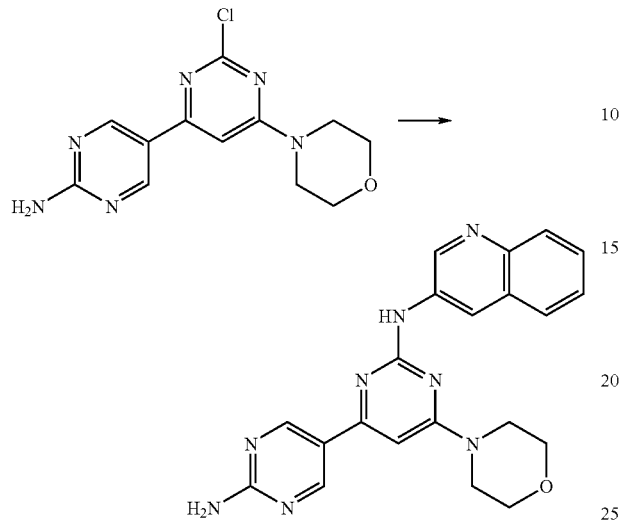

A mixture of 2-chloro-6-morpholino-4,5'-bipyrimidin-2'-amine (10 mg), 3-amino-quinoline (9.8 mg), Pd(OAc)₂ (1.5 mg), BINAP (6.3 mg), and cesium carbonate (15.5 mg) in THF (1 mL) was heated in a microwave at 110° C. for 10 minutes. The crude product was filtered and concentrated under reduced pressure. The product was purified by preparative HPLC to give 6-morpholino-N²-(quinolin-3-yl)-4,5'-bi-pyrimidine-2,2'-diamine. LCMS (m/z): 401.0 (MH⁺). Rt=1.83 min.

Examples 18-24

According to Example 17, the reaction of 2-chloro-6-morpholino-4,5'-bipyrimidin-2'-amine with different amines yielded the following compounds:

Example 18

2-(2H-benzo[b][1,4]oxazin-4(3H)-yl)-6-morpholino-4,5'-bi-pyrimidin-2'-amine. LCMS (m/z): 392.3 (MH⁺). Rt=1.95 min.

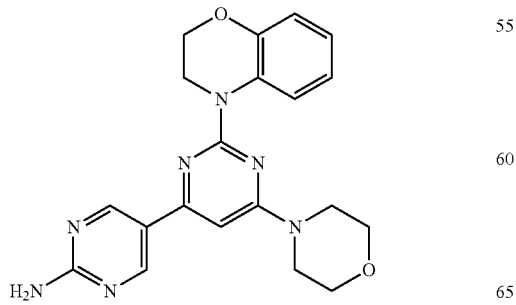

Example 19

6-morpholino-N²-(3-(trifluoromethyl)pyridin-4-yl)-4,5'-bi-pyrimidine-2,2'-diamine. LCMS (m/z): 419.1 (MH⁺). Rt=1.83 min.

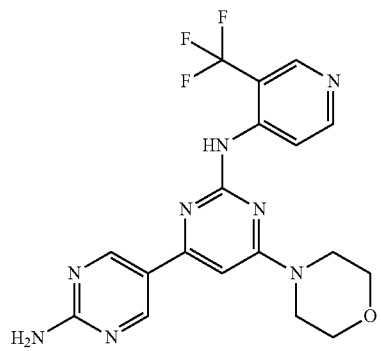

Example 20

7-(2'-amino-6-morpholino-4,5'-bipyrimidin-2-ylamino)-2H-benzo[b][1,4]oxazin-3(4H)-one. LCMS (m/z): 421.1 (MH⁺). Rt=1.70 min.

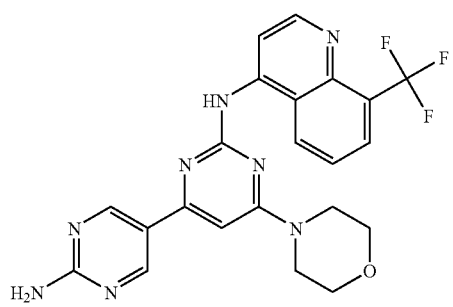

Example 21

6-morpholino-N²-(8-(trifluoromethyl)quinolin-4-yl)-4,5'-bi-pyrimidine-2,2'-diamine. LCMS (m/z): 469.1 (MH⁺). Rt=2.09 min.

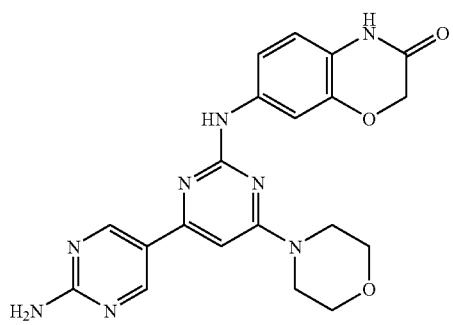

Example 22

2-(3,4-dihydroquinolin-1(2H)-yl)-6-morpholino-4,5'-bipyrimidin-2'-amine. LCMS (m/z): 390.1 (MH+). Rt=2.09 min.

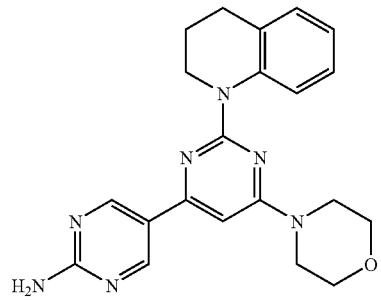

Example 23

6-morpholino-N²-(6-(piperazin-1-yl)pyridin-3-yl)-4,5'-bipyrimidine-2,2'-diamine. LCMS (m/z): 435.1 (MH+). Rt=1.50 min.

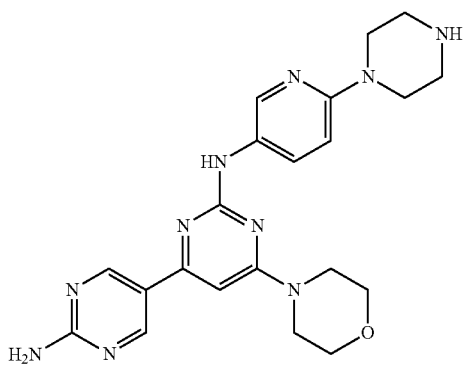

Example 24

N²-(6-(4-methylpiperazin-1-yl)pyridin-3-yl)-6-morpholino-4,5'-bipyrimidine-2,2'-diamine. LCMS (m/z): 449.1 (MH+). Rt=1.52 min.

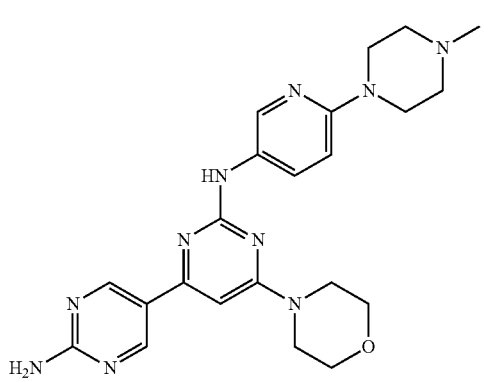

Example 25

Preparation of 6-morpholino-2-(tetrahydro-2H-pyran-4-yl)-4,5'-bipyrimidin-2'-amine

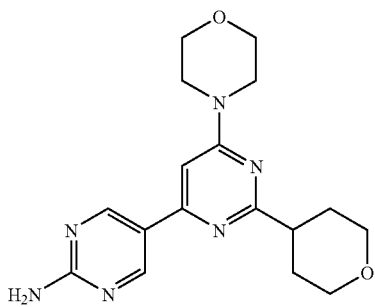

A mixture of 6-morpholino-2-(tetrahydro-2H-pyran-4-yl)-4,5'-bipyrimidin-2'-amine (10 mg, 0.0343 mmol), morpholine (24 mg, 8 equiv, 0.274 mmol) in NMP (0.55 mL) was heated at 150° C. for 10 min in a microwave. The mixture was purified on HPLC to give 6-morpholino-2-tetrahydro-2H-pyran-4-yl)-4,5'-bipyrimidin-2'-amine. LCMS (m/z): 343.1 (MH+). Rt: 1.62 min.

Examples 26-33

According to Example 17, the reaction of 2-chloro-N-methyl-6-morpholino-4,5'-bipyrimidin-2'-amine with different amines yielded following compounds:

Example 26

N²'-methyl-6-morpholino-N²-(6-(piperazin-1-yl)pyridin-3-yl)-4,5'-bipyrimidine-2,2'-diamine. LC MS (m/z): 449.2 (MH+). Rt=1.61 min.

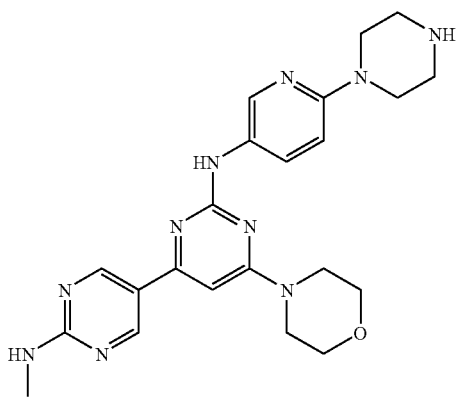

Example 27

N$^{2'}$-methyl-N$^{2'}$-(6-(4-methylpiperazin-1-yl)pyridin-3-yl)-6-morpholino-4,5'-bipyrimidine-2,2'-diamine. LC MS (m/z): 463.2 (MH$^+$). Rt=1.62 min.

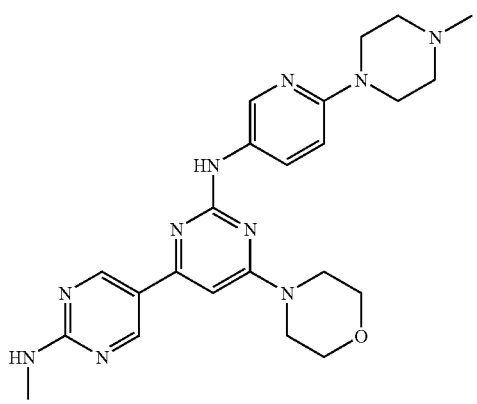

Example 28

2-(2H-benzo[b][1,4]oxazin-4(3H)yl)-N-methyl-6-morpholino-4,5'-bipyrimidin-2'-amine. LCMS (m/z): 406.1 (MH$^+$). Rt=2.30 min.

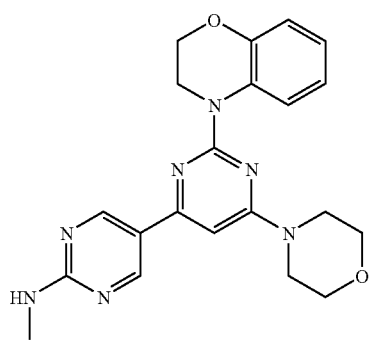

Example 29

N$^2$-(6-methoxyquinolin-3-yl)-N$^{2'}$-methyl-6-morpholino-4,5'-bipyrimidine-2,2'-diamine. LCMS (m/z): 445.5 (MH$^+$). Rt=2.01 min.

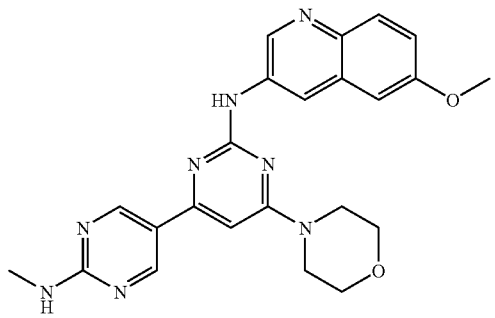

Example 30

N$^{2'}$-methyl-6-morpholino-N$^2$-(3-(trifluoromethyl)pyridin-4-yl)-4,5'-bipyrimidine-2,2'-diamine. LCMS (m/z): 433.1 (MH$^+$). Rt=1.95 min.

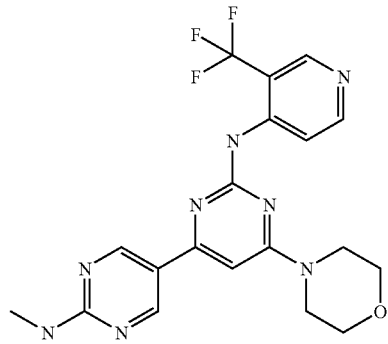

Example 31

7-(2'-(methylamino)-6-morpholino-4,5'-bipyrimidin-2-ylamino)-2H-benzo[b][1,4]oxazin-3(4H)-one. LCMS (m/z): 435.1 (MH$^+$). Rt=1.86 min.

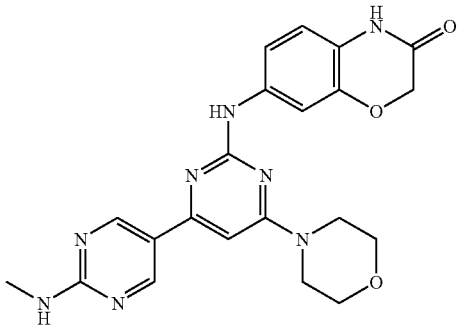

Example 32

N2'-methyl-6-morpholino-N2-(8-(trifluoromethyl)quinolin-4-yl)-4,5'-bipyrimidine-2,2'-diamine. LCMS (m/z): 483.1 (MH$^+$). Rt=2.21 min.

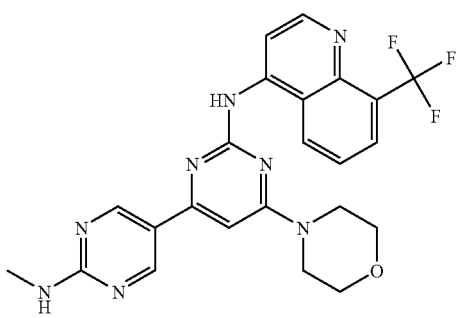

Example 33

2-(3,4-dihydroquinolin-1(2H)-yl)-N-methyl-6-morpholino-4,5'-bipyrimidin-2'-amine. LCMS (m/z): 404.2 (MH+). Rt=2.27 min.

Example 34

Biological Activity Screening Assays

Each of the compounds of Examples 1-33 were screened for biological activity according to Biological Method 1 (below), and exhibited an $IC_{50}$ value of less than about 25 µM with respect to inhibition of PI3K. Compounds of many of the Examples exhibited $IC_{50}$ values of less than about 10 µM, and less than about 1 µM, and even less than about 0.1 µM with respect to inhibition of PI3K. For this reason, each of the compounds is individually preferred and preferred as a member of a group.

Biological Method 1

Phosphorylation Assays

Assay 1: Homogenous Solution Phase Assay

Compounds to be tested are dissolved in DMSO and directly distributed into 384-well flashplates at 1.25 µL per well. To start the reaction, 20 µL of 6 nM PI3 kinase are added into each well followed by 20 µL of 400 nM ATP containing a trace of radiolabeled ATP and 900 nM 1-alpha-phosphatidylinositol (PI). The plates are briefly centrifuged to remove any air gap. The reaction is performed for 15 minutes and then stopped by the addition of 20 µL of 100 mM EDTA. The stopped reaction is incubated overnight at RT to allow the lipid substrate to bind by hydrophobic interaction to the surface of the flashplate. The liquid in the wells is then washed away, and the labeled substrate is detected with scintillation counting.

Assay 2: One Step Solid Phase Assay

This method is similar to Assay 1 except that the lipid substrate (1-alpha-phosphatidylinositol (PI)) is first dissolved in a coating buffer and incubated on flashplate at room temperature overnight to allow the lipid substrate to bind by hydrophobic interaction to the surface of the flashplate. Unbound substrate is then washed away. On the day of assay, 20 µL of 6 nM PI3 kinase are added into each well followed by 20 µL of 400 nM ATP containing trace of radiolabeled ATP. Compounds are added together with enzyme and ATP to the lipid-coated plates. The plates are briefly centrifuged to remove any air gap. The reaction is performed for two to three hours. The reaction is stopped by addition of 20 µL of 100 mM EDTA or by immediate plate washing. Phosphorylated lipid substrate is detected by scintillation counting.

Assay 3: ATP Depletion Assay

Compounds to be tested are dissolved in DMSO and directly distributed into a black 384-well plate at 1.25 µL per well. To start the reaction, 25 µL of 10 nM PI3 kinase and 5 µg/mL 1-alpha-phosphatidylinositol (PI) are added into each well followed by 25 µL of 2 µM ATP. The reaction is performed until approx 50% of the ATP is depleted, and then stopped by the addition of 25 µL of KinaseGlo solution. The stopped reaction is incubated for 5 minutes and the remaining ATP is then detected via luminescence.

Biological Method 2

$pSer^{473}$ Akt Assays to Monitor PI3K Pathway

In this method, an assay for measuring the PI3K-mediated $pSer^{473}$-Akt status after treatment with representative inhibitor compounds of the preferred embodiments is described.

A2780 cells were cultured in DMEM supplemented with 10% FBS. L-glutamine, sodium pyruvate, and antibiotics. Cells were plated in the same medium at a density of 15,000 cells per well into 96 well tissue culture plates, with outside wells vacant, and allowed to adhere overnight.

Test compounds supplied in DMSO were diluted further into DMSO at 500 times the desired final concentrations before dilution into culture media to 2 times the final concentrations. Equal volumes of 2× compounds were added to the cells in 96 well plates and incubated at 37° C. for one hour. The media and compounds were then removed, the plates chilled and cells lysed in a lysis buffer (150 mM NaCl, 20 mM Tris pH 7.5, 1 mM EDTA, 1 mM EGTA, 1% Triton X-100) supplemented with phosphatase and protease inhibitors. After thorough mixing, lysates were transferred to both pSer473Akt and total Akt assay plates from Meso Scale Discovery (MSD), and incubated overnight with shaking at 4° C. The plates were washed with 1×MSD wash buffer and the captured analytes detected with secondary antibodies. After incubation with the secondary antibody at room temperature for 1-2 hours, the plates were washed again and 1.5× concentration of Read Buffer T (MSD) was added to the wells.

The assays were read on a SECTOR Imager 6000 instrument (Meso Scale Discovery). Ratios of the signal from $pSer^{473}$Akt and total Akt assays were used to correct for any variability and the percent inhibition of $pSer^{473}$Akt from the total signal seen in cells treated with compound versus DMSO alone was calculated and used to determine $EC_{50}$ values for each compound.

All of the references cited herein are hereby incorporated by reference in their entirety.

While illustrative embodiments have been illustrated and described, it will be appreciated that various changes can be made therein without departing from the spirit and scope of the invention.

What is claimed is:

1. A compound of Formula I, or a tautomer, or pharmaceutically acceptable salt thereof,

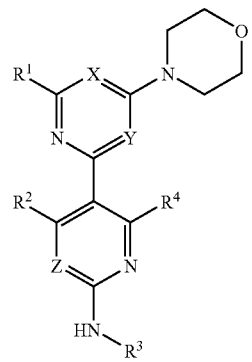

(I)

wherein,
X is N and Y is CH, or Y is N and X is CH;
Z is N or CH;
$R^1$ is selected from the group consisting of morpholino, tetrahydropyranyloxy and methoxypyridinylamino, provided that when X is N, $R^1$ is not morpholino;

R² is selected from the group consisting of trifluoromethyl, amino and oxo and R⁴ is hydrogen; and R³ is hydrogen.

2. A compound of claim 1 wherein Y is N and X is CH.

3. A compound of claim 2 wherein Z is N.

4. A compound of claim 2 wherein Z is CH.

5. A compound of claim 2 selected from the group consisting of 5-(4-morpholino-6-(tetrahydro-2H-pyran-4-yloxy)pyrimidin-2-yl)-4-(trifluoromethyl)pyridin-2-amine, 4-morpholino-6-(tetrahydro-2H-pyran-4-yloxy)-4'-(trifluoromethyl)-2,5'-bipyrimidin-2'-amine, 4-morpholino-6-(tetrahydro-2H-pyran-4-yloxy)-2,5'-bipyrimidine-2',4'-diamine, 2-amino-5-(4-morpholino-6-(tetrahydro-2H-pyran-4-yloxy)pyrimidin-2-yl)pyrimidin-4(3H)-one, 2-(6-amino-4-(trifluoromethyl)pyridin-3-yl)-N-(6-methoxypyridin-3-yl)-6-morpholinopyrimidin-4-amine, N4-(6-methoxypyridin-3-yl)-6-morpholino-4'-(trifluoromethyl)-2,5'-bipyrimidine-2',4-diamine, N4-(6-methoxypyridin-3-yl)-6-morpholino-2,5'-bipyrimidine-2',4,4'-triamine, 2-amino-5-(4-(6-methoxypyridin-3-ylamino)-6-morpholinopyrimidin-2-yl)pyrimidin-4(3H)-one, 5-(4,6-dimorpholino-pyrimidin-2-yl)-4-(trifluoromethyl)pyridin-2-amine, 4,6-dimorpholino-4'-(trifluoro-methyl)-2,5'-bipyrimidin-2'-amine, 4,6-dimorpholino-2,5'-bipyrimidine-2',4'-diamine, and the tautomers, and pharmaceutically acceptable salts thereof.

6. A pharmaceutical composition comprising a pharmaceutically acceptable carrier and a therapeutically effective amount of a compound of Formula I, or a tautomer, or pharmaceutically acceptable salt thereof.

* * * * *